(12) United States Patent
Linker et al.

(10) Patent No.: US 6,743,755 B2
(45) Date of Patent: Jun. 1, 2004

(54) SUBSTITUTED N-ARYL NITROGEN-CONTAINING HETEROCYCLIC COMPOUNDS

(75) Inventors: Karl-Heinz Linker, Leverkusen (DE); Kurt Findeisen, Leverkusen (DE); Otto Schallner, Monheim (DE); Andreas Lender, Wuppertal (DE); Hans-Joachim Santel, Leverkusen (DE); Markus Dollinger, Leverkusen (DE); Akihiko Yanagi, Tochigi (JP); Toshio Goto, Kokubunji-machi (JP)

(73) Assignee: Bayer Aktiengesellschaft, Leverkusen (DE)

( * ) Notice: Subject to any disclaimer, the term of this patent is extended or adjusted under 35 U.S.C. 154(b) by 78 days.

(21) Appl. No.: 10/138,011

(22) Filed: May 2, 2002

(65) Prior Publication Data

US 2003/0144522 A1 Jul. 31, 2003

Related U.S. Application Data

(62) Division of application No. 09/667,392, filed on Sep. 20, 2000, now Pat. No. 6,426,318, which is a division of application No. 09/245,818, filed on Feb. 5, 1999, now Pat. No. 6,162,765, which is a division of application No. 08/849,966, filed as application No. PCT/EP95/04759 on Dec. 4, 1995, now abandoned.

(30) Foreign Application Priority Data

Dec. 15, 1994 (DE) ............................................ 44 44 741
Aug. 24, 1995 (DE) .......................................... 195 31 152

(51) Int. Cl.$^7$ ......................... A01N 43/84; C07D 413/04

(52) U.S. Cl. ....................................... 504/225; 544/105

(58) Field of Search ........................... 504/225; 544/105

(56) References Cited

U.S. PATENT DOCUMENTS

| | | | |
|---|---|---|---|
| 3,912,735 A | 10/1975 | Von Bredow et al. | |
| 4,087,534 A | 5/1978 | Ovadia et al. | |
| 4,326,878 A | 4/1982 | Ziman | |
| 4,366,320 A | 12/1982 | Gilbertson | |
| 4,452,981 A | 6/1984 | Nagano et al. | |
| 4,593,094 A | 6/1986 | Nagano et al. | |
| 4,789,394 A | 12/1988 | Bohner et al. | |
| 5,108,486 A | 4/1992 | Kondo et al. | |
| 6,162,765 A | * 12/2000 | Linker et al. | ................ 504/225 |

FOREIGN PATENT DOCUMENTS

| | | |
|---|---|---|
| EP | 0 011 693 | 6/1980 |
| GB | 2 041 353 | 9/1980 |
| GB | 2 055 926 | 3/1981 |
| GB | 2 063 855 | 6/1981 |

OTHER PUBLICATIONS

Journal of Pharmaceutical Sciences, vol. 82, No. 4, Apr. 4, 1993, Washington, D.C., pp. 408–415, R. Simlot et al. "Synthesis and hypolipidemic activity of 4–sustituted 1–acyl–1,2,4–triazolidine–3,5–diones in rodents".

Chemical Abstracts, vol. 89, No. 3, Jul. 17, 1978, Columbus, Ohio, Abstract No. 24319z, p. 653.

Stadler et al., "Ionomer Model System . . . ", CA 110–24377 (1989).

Gilbertson et al., "A Convenient Synthesis of Fluorinated Phenyl–1,2,4–triazoline–3,5–diones", CA 96:199596 (1982).

Shigematsu et al., "3,5–dichloro–4–fluorophenyl- isocyanate", (1979), CA 91:39115.

Cram & Hammond, "Organic Chemistry", McGraw–Hill Book Co., N.Y. (1964), 2$^{nd}$ Ed., pp. 565–567.

* cited by examiner

*Primary Examiner*—Patricia L. Morris
(74) *Attorney, Agent, or Firm*—Norris McLaughlin & Marcus

(57) ABSTRACT

The invention relates to novel substituted N-aryl nitrogen-containing heterocyclic compounds of the general formula (I)

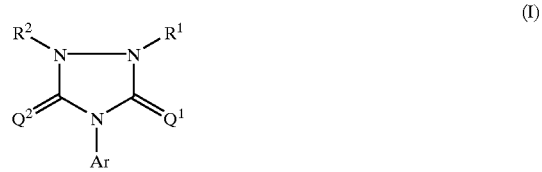

(I)

and to the compounds isomeric to the substituted N-aryl nitrogen-containing heterocyclic compounds of the formula (I), of the formulae (Ia) and (Ib)

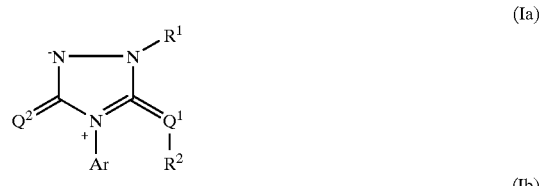

(Ia)

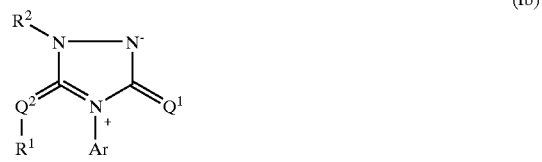

(Ib)

in which $Q^1$, $Q^2$, $R^1$, $R^2$ and Ar have the meanings given in the description, processes for their preparation and their use as herbicides.

5 Claims, No Drawings

SUBSTITUTED N-ARYL NITROGEN-CONTAINING HETEROCYCLIC COMPOUNDS

This application is a divisional of application Ser. No. 09/667,392, which was filed on Sep. 20, 2000, now U.S. Pat. No. 6,426,318, which is a divisional of application Ser. No. 09/245,818, which was filed on Feb. 5, 1999, now U.S. Pat. No. 6,162,765, which is a divisional of application Ser. No. 08/849,966, filed on Jun. 6, 1997, now abandoned, which was filed under 35 U.S.C. 371 and based on PCT/EP95/04759, filed on Dec. 4, 1995.

The invention relates to novel substituted N-aryl nitrogen-containing heterocyclic compounds, processes for their preparation and their use as herbicides.

It is known that certain N-aryl nitrogen-containing heterocyclic compounds have herbicidal properties (cf. EP 11693, DE 2952685, DE 3026739, U.S. Pat. Nos. 4,276,420, 4,326,878, WO 94/14817). However, the compounds known from the patent applications mentioned have not acquired noteworthy importance.

The novel substituted N-aryl nitrogen-containing heterocyclic compounds of the general formula (I)

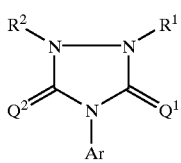
(I)

in which
- $Q^1$ represents oxygen or sulfur,
- $Q^2$ represents oxygen or sulfur,
- $R^1$ represents hydrogen, cyano or formyl or represents alkyl which is optionally substituted by halogen, cyano, carboxyl, alkoxy, alkenyloxy, alkinyloxy, alkylthio, alkenylthio, alkinylthio, alkoxycarbonyl, alkenyloxycarbonyl or alkinyloxycarbonyl,
- $R^1$ furthermore represents alkenyl or alkinyl, in each case optionally substituted by halogen,
- $R^1$ furthermore represents alkylcarbonyl, alkenylcarbonyl, alkinylcarbonyl, alkoxycarbonyl, alkenyloxycarbonyl or alkinyloxycarbonyl, in each case optionally substituted by halogen,
- $R^1$ furthermore represents cycloalkyl or cycloalkylcarbonyl, in each case optionally substituted by halogen, cyano or carboxyl,
- $R^2$ represents hydrogen, cyano or formyl, or represents alkyl which is optionally substituted by halogen, cyano, carboxyl, alkoxy, alkenyloxy, alkinyloxy, alkylthio, alkenylthio, alkinylthio, alkoxycarbonyl, alkenyloxycarbonyl or alkinyloxycarbonyl,
- $R^2$ furthermore represents alkenyl or alkinyl, in each case optionally substituted by halogen,
- $R^2$ furthermore represents alkylcarbonyl, alkenylcarbonyl, alkinylcarbonyl, alkoxycarbonyl, alkenyloxycarbonyl or alkinyloxycarbonyl, in each case optionally substituted by halogen,
- $R^2$ furthermore represents cycloalkyl or cycloalkylcarbonyl, in each case optionally substituted by halogen, cyano or carboxyl, and
- Ar represents the substituted monocyclic or bicyclic aryl or heteroaryl grouping defined below.

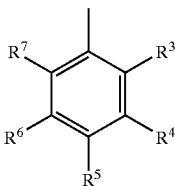

in which
- $R^3$ represents hydrogen or halogen,
- $R^4$ represents hydrogen or halogen,
- $R^5$ represents cyano, carboxyl, chlorocarbonyl, carbamoyl, thiocarbamoyl, hydroxyl or halogen, or represents alkyl, alkoxy or alkoxycarbonyl, in each case optionally substituted by halogen,
- $R^6$ represents the following grouping $$-A^1-A^2-A^3$$

in which
- $A^1$ represents a single bond, or represents oxygen, sulfur, —SO—, —SO$_2$—, —CO— or the grouping —N—A$^4$—, in which A$^4$ represents hydrogen, hydroxyl, alkyl, alkenyl, alkinyl, alkoxy, aryl, alkylcarbonyl, arylcarbonyl, alkylsulfonyl or arylsulfonyl,
- $A^1$ furthermore represents alkanediyl, alkenediyl, azaalkenediyl, alkinediyl, cycloalkanediyl, cycloalkenediyl or phenylene, in each case optionally substituted by halogen,
- $A^2$ represents a single bond, or represents oxygen, sulfur, —SO—, —SO$_2$—, —CO— or the grouping —N—A$^4$—, in which A$^4$ represents hydrogen, hydroxyl, alkyl, alkoxy, aryl, alkylsulfonyl or arylsulfonyl,
- $A^2$ furthermore represents alkanediyl, alkenediyl, azaalkenediyl, alkinediyl, cycloalkanediyl, cycloalkenediyl or phenylene, in each case optionally substituted by halogen,
- $A^3$ represents hydrogen, with the proviso that in this case $A^1$ and/or $A^2$ do(es) not represent any single bond,
- $A^3$ furthermore represents hydroxyl, mercapto, amino, cyano, isocyano, thiocyanato, nitro, carboxyl, carbamoyl, thiocarbamoyl, sulfo, chlorosulfonyl or halogen, or represents alkyl, alkoxy, alkylthio, alkylsulfinyl, alkylsulfonyl, alkylamino, dialkylamino, alkoxycarbonyl or dialkoxy-(thio) phosphoryl, in each case optionally substituted by halogen or alkoxy,
- $A^3$ furthermore represents alkenyl alkenyloxy, alkenylthio, alkenylamino, alkylidenamino, alkenyloxycarbonyl, alkinyl, alkinyloxy, alkinylthio, alkinylamino or alkinyloxycarbonyl, in each case optionally substituted by halogen,
- $A^3$ furthermore represents cycloalkyl, cycloalkyloxy, cycloalkylalkyl, cycloalkylalkoxy, cycloalkylidenamino, cycloalkyloxycarbonyl or cycloalkylalkoxycarbonyl, in each case optionally substituted by halogen, cyano, carboxyl, alkyl and/or alkoxy-carbonyl,
- $A^3$ furthermore represents aryl, aryloxy, aralkyl, arylalkoxy, aryloxycarbonyl or arylalkoxycarbonyl, in each case optionally substituted by nitro, cyano, carboxyl, halogen, alkyl, halogenalkyl, alkyloxy, halogenalkyloxy and/or alkoxy-carbonyl, A³ furthermore represents m each case optionally completely or partly hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolylalkyl, furylalkyl, thienylalkyl, oxazolylalkyl, isoxazolylalkyl, thiazolylalkyl, pyridinylalkyl, pyrimidinylalkyl, pyrazolylalkoxy or furylalkoxy, or represents perhydropyranylalkoxy or pyridylalkoxy, and R⁷ represents hydrogen or halogen, or in each case two adjacent radicals —R³ and R⁴, R⁴ and R⁵, R⁵ and R⁶ or R⁶ and R⁷— together represent one of the following groupings —Q³—CQ⁴—, —Q³—CQ⁴—Q⁵—, —Q³—C(R⁸,R⁹)—Q⁵—, —C(R⁸,R⁹)—CQ⁴—, —C(R⁸,R⁹)—Q³—CQ⁴—, —Q³—C(R⁸,R⁹)—C(R⁸,R⁹)—, —Q³—C(R⁸,R⁹)—C(R⁸,R⁹)—Q⁵—, —C(R⁸,R⁹)—C(R⁸,R⁹)—CQ⁴—, —Q³—C(R⁸)=C(R⁸)—, —C(R⁸)=C(R⁸)—CQ⁴—, —Q³—C(R⁸,R⁹)—CQ⁴—, —N(R¹⁰)—C(R⁸,R⁹)—CQ⁴—, —C(R⁸)=N—, —Q³—CQ⁴—C(R⁸,R⁹)—, —Q³—CQ⁴—N(R¹⁰)—, —Q³—C(R⁸,R⁹)—CQ⁴—N(R¹⁰)—, —CR⁸, R⁹)—Q³—CQ⁴—N(R¹⁰)—, —C(R⁸,R⁹)—C(R⁸,R⁹)—N(R¹⁰)—, —C(R⁸,R⁹)—C(R⁸,R⁹)—CQ⁴—N(R¹⁰)—, —C(R⁸)=C(R⁸)—N(R¹⁰)—, —C(R⁸)=C(R⁸)—CQ⁴—N(R¹⁰)—, —C(R⁸,R⁹)—CQ⁴—N(R¹⁰)—, —N(R¹⁰)—C(R⁸,R⁹)—CQ⁴—N(R¹⁰)—, —C(R⁸)=N—N(R¹⁰)—, —Q³C—Q⁴—C(R⁸,R⁹)—N(R¹⁰)—, Q³—C(R⁸,R⁹)—(R⁸,R⁹)—CQ⁴—N(R¹⁰)— in which

Q³, Q⁴ and Q⁵ are identical or different and in each case represent oxygen or sulfur, R⁸ and R⁹ are identical or different and individually represent hydrogen, halogen or alkyl or together represent alkanediyl, and R¹⁰ represents hydrogen or hydroxyl, or represents alkyl, alkylcarbonyl, alkoxycarbonyl or alkylsulfonyl which are optionally substituted by cyano, halogen, alkoxy, alkyl-carbonyl or alkoxy-carbonyl, or represents alkenyl or alkinyl, in each case optionally substituted by halogen, or represents cycloalkyl or cycloalkylalkyl, in each case optionally substituted by halogen or alkyl, or represents alkoxy or alkenyloxy, in each case optionally substituted by halogen, or represents arylalkyl or arylalkoxy, in each case optionally substituted by cyano, halogen, alkyl, halogenoalkyl, alkoxy or halogenoalkoxy, have now been found, the already known compounds 4-(3,4-dichlorophenyl)-1,2-dimethyl-5-thioxo-1,2,4-triazolidin-3-one and 4-(4-chloro-3-trifluoromethylphenyl)-1,2-dimethyl-5-thioxo-1,2,4-triazolidin-3-one (cf. DE 2952685 and DE 3026739) being excluded by disclaimer.

The compounds isomeric to the substituted N-aryl nitrogen-containing heterocyclic compounds of the formula (I), of the formulae (Ia) and (Ib)

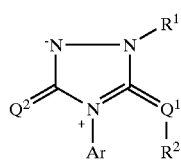

(Ia)

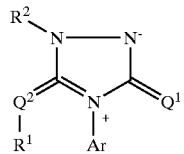

(Ib)

in which

Q¹, Q², R¹, R² and Ar have the abovementioned meanings, have furthermore also been found The novel substituted N-aryl nitrogen-containing heterocyclic compounds of the general formula (I) and, where appropriate, the compounds of the formulae (Ia) or (Ib) are obtained when (a) (thio)semicarbazide derivatives of the general formula (II)

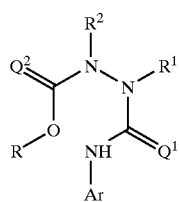

(II)

in which

Q¹, Q², R¹, R² and Ar have the abovementioned meanings and

R represents alkyl, are subjected to a cyclizing condensation reaction, if appropriate in the presence of a reaction auxiliary and if appropriate in the presence of a diluent, and thereafter, if appropriate, electrophilic or nucleophilic substitution reactions are carried out in the customary manner in the context of the definition of the substituents, or when (b) aryliminoheterocyclic compounds of the general formula (III)

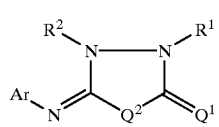

(III)

in which

Q¹, Q², R¹, R² and Ar have the abovementioned meanings, —or compounds of the formula (Ia) or (Ib)—above— are isomerized thermally ("pyrolytically"), if appropriate in the presence of a reaction auxiliary and if appropriate in the presence of a diluent The compounds of the formula (I) can in principle also be synthesized as shown schematically below:

(c) reaction of aryl iso(thio)cyanates of the formula (IV) with hydrazines of the formula (V) to give aryl(thio)semicarbazides of the formula (VI) and reaction thereof with (thio)phosgene:

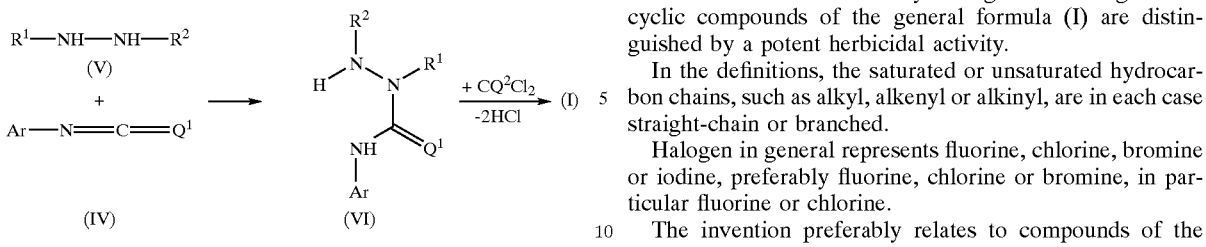

(d) reaction of aryl iso(thio)cyanates of the formula (IV) with S-alkyldithiocarbazates of the formula (VII) and subsequent cyclizing condensation:

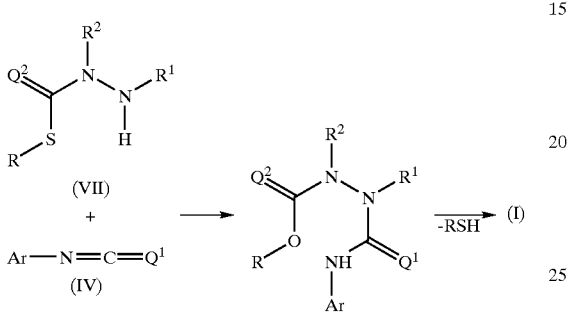

(e) reaction of N,N-bis-chlorocarbonyl- or N,N-bis-phenoxycarbonyl-arylamines of the formula (VIII)—Y:Cl or $OC_6H_5$— with hydrazines of the formula (V):

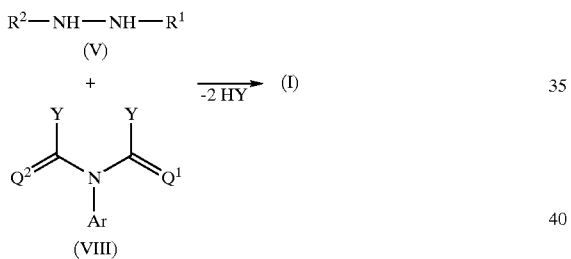

(f) reaction of arylamines of the formula (IX) with hydrazinedicarboxylic acid esters of the formula (X):

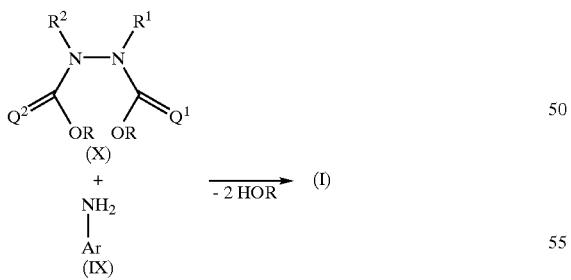

The compounds of the general formula (I) can also be converted into other compounds of the general formula (I) according to the above definition by further customary methods, for example by customary conversions of carboxylic acid groupings or derivatives thereof (for example $R^5$: COOH→COCl, COOH→$COOCH_3$, COCl→$CONH_2$, $COOCH_3$→$CONH_2$, $CONH_2$→CN, CN→$CSNH_2$), by alkylation reactions (for example $R^1$:H→$CH_3$ or $CHF_2$) or by oxidation or sulfurization (for example $Q_1$: O→S or S→O)— cf. also the preparation examples.

The novel substituted N-aryl nitrogen-containing heterocyclic compounds of the general formula (I) are distinguished by a potent herbicidal activity.

In the definitions, the saturated or unsaturated hydrocarbon chains, such as alkyl, alkenyl or alkinyl, are in each case straight-chain or branched.

Halogen in general represents fluorine, chlorine, bromine or iodine, preferably fluorine, chlorine or bromine, in particular fluorine or chlorine.

The invention preferably relates to compounds of the formulae (I), (Ia) and (Ib) in which $Q^1$ represents oxygen or sulfur, $Q^2$ represents oxygen or sulfur, $R^1$ represents hydrogen, cyano or formyl, or represents $C_1$–$C_6$-alkyl, in each case optionally substituted by fluorine, chlorine, cyano, carboxyl, $C_1$–$C_4$-alkoxy, $C_3$–$C_4$-alkenyloxy, $C_3$–$C_4$-alkinyloxy, $C_1$–$C_4$-alkylthio, $C_3$–$C_4$-alkenylthio, $C_3$–$C_4$-alkinylthio, $C_1$–$C_4$-alkoxy-carbonyl, $C_3$–$C_4$-alkenyloxy-carbonyl or $C_3$–$C_4$-alki-nyloxy-carbonyl, $R^1$ furthermore represents $C_3$–$C_6$-alkenyl or $C_3$–$C_6$-alkinyl, in each case optionally substituted by fluorine or chlorine, $R^1$ furthermore represents $C_1$–$C_6$-alkyl-carbonyl, $C_3$–$C_6$-alkenyl-carbonyl, $C_3$–$C_6$-alkinyl-carbonyl, $C_1$–$C_6$-alkoxy-carbonyl, $C_1$–$C_6$-alkenyloxy-carbonyl or $C_3$–$C_6$-alkinyloxy-carbonyl, in each case optionally substituted by fluorine or chlorine, $R^1$ furthermore represents $C_3$–$C_6$-cycloalkyl or $C_3$–$C_6$-cycloalkyl-carbonyl, in each case optionally substituted by fluorine, chlorine, bromine, cyano or carboxyl, $R^2$ represents hydrogen, cyano or formyl, or represents $C_1$–$C_6$-alkyl, in each case optionally substituted by fluorine, chlorine, cyano, carboxyl, $C_1$–$C_4$-alkoxy, $C_3$–$C_4$-alkenyloxy, $C_3$–$C_4$-alkinyloxy, $C_1$–$C_4$-alkylthio, $C_3$–$C_4$-alkenylthio, $C_3$–$C_4$-alkinylthio, $C_1$–$C_4$-alkoxy-carbonyl, $C_3$–$C_4$-alkenyloxy-carbonyl or $C_3$–$C_4$-alki-nyloxy-carbonyl, $R^2$ furthermore represents $C_3$–$C_6$-alkenyl or $C_3$–$C_6$-alkenyl, in each case optionally substituted by fluorine or chlorine, $R^2$ furthermore represents $C_1$–$C_6$-alkyl-carbonyl, $C_3$–$C_6$-alkenyl-carbonyl, $C_3$–$C_6$-alkinyl-carbonyl, $C_1$–$C_6$-alkoxy-carbonyl, $C_3$–$C_6$-alkenyloxy-carbonyl or $C_3$–$C_6$-alkinyloxy-carbonyl, in each case optionally substituted by fluorine or chlorine, $R^2$ furthermore represents $C_3$–$C_6$-cycloalkyl or $C_3$–$C_6$-cycloalkyl-carbonyl, in each case optionally substituted by fluorine, chlorine, bromine, cyano or carboxyl, and Ar represents the substituted monocyclic or bicyclic aryl or heteroaryl grouping defined below

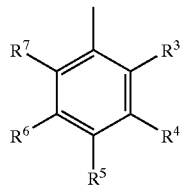

in which $R^3$ represents hydrogen, fluorine, chlorine or bromine, $R^4$ represents hydrogen, fluorine, chlorine or bromine, $R^5$ represents cyano, carboxyl, chlorocarbonyl, carbamoyl, thiocarbamoyl, hydroxyl, fluorine, chlorine, bromine or represents alkyl, alkoxy or alkoxycarbonyl having in each case up to 4 carbon atoms and in each case optionally substituted by fluorine and/or chlorine, $R^6$ represents the following grouping $$-A^1-A^2-A^3$$

in which $A^1$ represents a single bond, or represents oxygen, sulfur, —SO—, —SO$_2$—, —CO— or the grouping —N—A$^4$—, in which A$^4$ represents hydrogen, hydroxyl, $C_1$–$C_4$-alkyl, $C_3$–$C_4$-alkenyl, $C_3$–$C_4$-alkinyl, $C_1$–$C_4$-alkoxy, phenyl, $C_1$–$C_4$-alkyl-carbonyl, phenylcarbonyl, $C_1$–$C_4$-alkyl-sulfonyl or phenylsulfonyl, $A^1$ furthermore represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, in each case optionally substituted by fluorine, chlorine or bromine, $A^2$ represents a single bond, or represents oxygen, sulfur, —SO—, —SO$_2$—, —CO— or the grouping —N—A$^4$—, in which A$^4$ represents hydrogen, hydroxyl, $C_1$–$C_4$-alkyl, $C_1$–$C_4$-alkoxy, phenyl, $C_1$–$C_4$-alkylsulfonyl or phenylsulfonyl, $A^2$ furthermore represents $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, in each case optionally substituted by fluorine, chlorine or bromine, $A^3$ represents hydrogen, with the proviso that in this case $A^1$ and/or $A^2$ do(es) not represent a single bond, $A^3$ furthermore represents hydroxyl, mercapto, amino, cyano, isocyano, thiocyanato, nitro, carboxyl, carbamoyl, thiocarbamoyl, sulfo, chlorosulfonyl, fluorine, chlorine or bromine, $A^3$ furthermore represents alkyl, alkoxy, alkylthio, alkylsulfinyl, alkylsulfonyl, alkylamino, dialkylamino, alkoxycarbonyl or dialkoxy(thio)phosphoryl having in each case 1 to 6 carbon atoms in the alkyl groups and in each case optionally substituted by fluorine, chlorine or $C_1$–$C_4$-alkoxy, $A^3$ furthermore represents alkenyl, alkenyloxy, alkenylamino, alkylidenamino, alkenyloxycarbonyl, alkinyl, alkinyloxy, alkinylamino or alkinyloxycarbonyl having in each case 2 to 6 carbon atoms in the alkenyl, alkylidene or alkinyl groups and in each case optionally substituted by fluorine or chlorine, $A^3$ furthermore represents cycloalkyl, cycloalkyloxy, cycloalkylalkyl, cycloalkylalkoxy, cycloalkylidenamino, cycloalkyloxycarbonyl or cycloalkylalkoxycarbonyl having in each case 3 to 6 carbon atoms in the cycloalkyl groups and where appropriate 1 to 4 carbon atoms in the alkyl groups and in each case optionally substituted by fluorine, chlorine, cyano, carboxyl, $C_1$–$C_4$-alkyl and/or $C_1$–$C_4$-alkoxycarbonyl, $A^3$ furthermore represents phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, in each case optionally substituted by nitro, cyano, carboxyl, fluorine, chlorine, bromine, $C_1$–$C_4$-alkyl, $C_1$–$C_4$-halogenalkyl, $C_1$–$C_4$-alkyloxy, $C_1$–$C_4$-halogenalkyloxy and/or $C_1$–$C_4$-alkoxy-carbonyl, $A^3$ furthermore represents in each case optionally completely or partly hydrogenated pyrrolyl, pyrazolyl, imidazolyl, triazolyl, furyl, oxiranyl, oxetanyl, dioxolanyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazolyl-$C_1$–$C_4$-alkyl, thiazolyl-$C_1$–$C_4$-alkyl, pyridinyl-$C_1$–$C_4$-alkyl, pyrimidinyl-$C_1$–$C_4$-alkyl, pyrazolylmethoxy or furylmethoxy, or represents perhydropyranylmethoxy or pyridylmethoxy, and $R^7$ represents hydrogen, fluorine or chlorine, or in each case two adjacent radicals —$R^3$ and $R^4$, $R^4$ and $R^5$, $R^5$ and $R^6$ or $R^6$ and $R^7$— together represent one of the following groupings —Q$^3$—CQ$^4$—, —Q$^3$—CQ$^4$—Q$^5$—, —Q$^3$—C(R$^8$, R$^9$)—Q$^5$—, —C(R$^8$,R$^9$)—CQ$^4$—, —C(R$^8$,R$^9$)—Q$^3$—CQ$^4$—, —Q$^3$—C(R$^8$,R$^9$)—C(R$^8$,R$^9$)—, Q3—C(R$^8$,R$^9$)—C(R$^8$,R$^9$)—Q$^5$—, —C(R$^8$,R$^9$)—C(R$^8$,R$^9$)—CQ$^4$—,—Q$^3$—C(R$^8$)=C(R$^8$)—, —C(R$^8$)=C(R$^8$)—CQ$^4$—, —Q$^3$—C(R$^8$,R$^9$)—CQ$^4$—, —N(R$^{10}$)—C(R$^8$,R$^9$)—, CQ$^4$—, —C(R$^8$)=N—, —Q$^3$—CQ$^4$—C(R$^8$,R$^9$)—, —Q$^3$—CQ$^4$—(R$^{10}$)—, —Q$^3$—C(R$^8$,R$^9$)—CQ$^4$—N(R$^{10}$)—, —C(R$^8$,R$^9$)—Q$^3$—CQ$^4$—N(R$^{10}$)—, —C(R$^8$,R$^9$)—C(R$^8$, R$^9$)—N(R$^{10}$)—, —C(R$^8$,R$^9$)—C(R$^8$,R$^9$)—CQ$^4$—N(R$^{10}$)—, —C(R$^8$)=C(R$^8$)—N(R$^{10}$)—, —C(R$^8$)=C(R$^8$)—CQ$^4$—N(R$^{10}$)—, —C(R$^8$,R$^9$)—CQ$^4$—N(R$^{10}$)—, N(R$^{10}$)—C(R$^8$,R$^9$)—CQ$^4$—N(R$^{10}$)—, —C(R$^8$)=N—N(R$^{10}$)—, —Q$^3$—CQ$^4$—C(R$^8$,R$^9$)—N(R$^{10}$)—, —Q$^3$—C(R$^8$,R$^9$)—C(R$^8$,R$^9$)—CQ$^4$—N(R$^{10}$)

in which $Q^3$, $Q^4$ and $Q^5$ are identical or different and in each case represent oxygen or sulfur, $R^8$ and $R^9$ are identical or different and individually represent oxygen, fluorine, chlorine, bromine or $C_1$–$C_4$-alkyl or together represent $C_2$–$C_5$-alkanediyl, and $R^{10}$ represents hydrogen or hydroxyl, or represents alkyl, alkylcarbonyl, alkoxycarbonyl or alkylsulfonyl having in each case 1 to 6 carbon atoms in the alkyl groups and in each case optionally substituted by cyano, fluorine, chlorine, $C_1$–$C_4$-alkoxy, $C_1$–$C_4$-alkylcarbonyl or $C_1$–$C_4$-alkoxy-carbonyl, $R^{10}$ furthermore represents alkenyl or alkinyl having in each case 2 to 6 carbon atoms and in each case optionally substituted by fluorine, chlorine or bromine, $R^{10}$ furthermore represents cycloalkyl or cycloalkylalkyl having in each case 3 to 6 carbon atoms in the cycloalkyl groups and where appropriate 1 to 3 atoms in the alkyl group and in each case optionally substituted by fluorine, chlorine, bromine or $C_1$–$C_4$-alkyl, $R_{10}$ furthermore represents alkoxy or alkenyloxy having in each case up to 6 carbon atoms and in each case optionally substituted by fluorine and/or chlorine, and $R^{10}$ furthermore represents benzyl or benzyloxy, in each case optionally substituted by cyano, fluorine, chlorine, $C_1$–$C_4$-alkyl, $C_1$–$C_4$-halogenoalkyl, $C_1$–$C_4$-alkoxy or $C_1$–$C_4$-halogenoalkoxy, the already known compounds 4-(3,4-dichloro-phenyl)-1,2-dimethyl-5-thioxo-1,2,4-triazolidin-3-oneand4-(4-chloro-3-trifluoromethyl-phenyl)-1,2-dimethyl-5-thioxo-1,2,4-triazolidin-3-one (cf. DE 2952685 and DE 3026739) being excluded by disclaimer.

The invention particularly relates to compounds of the formulae (I), (Ia) and (Ib) in which $Q^1$ represents oxygen or sulfur, $Q^2$ represents oxygen or sulfur, $R^1$ represents hydrogen, cyano or formyl, or represents methyl, ethyl, n- or i-propyl or n-, i-, s- or t-butyl, in each case optionally substituted by fluorine, chlorine, cyano, carboxyl, methoxy or ethoxy, $R^1$ furthermore represents propenyl, butenyl, propinyl or butinyl, in each case optionally substituted by fluorine or chlorine, $R^1$ furthermore represents acetyl, propionyl, methoxycarbonyl or ethoxycarbonyl, in each case optionally substituted by fluorine or chlorine, $R^1$ furthermore represents cyclopropyl which is optionally substituted by fluorine or chlorine, $R^2$ represents hydrogen, cyano or formyl, or represents methyl, ethyl, n- or i-propyl or n-, i-, s- or t-butyl, in each case optionally substituted by fluorine, chlorine, cyano, carboxyl, methoxy or ethoxy, $R^2$ furthermore represents propenyl, butenyl, propinyl or butinyl, in each case optionally substituted by fluorine or chlorine, $R^2$ furthermore represents acetyl, propionyl, methoxycarbonyl or ethoxycarbonyl, in each case optionally substituted by fluorine or chlorine, $R^2$ furthermore represents cyclopropyl which is optionally substituted by fluorine or chlorine, and Ar represents the substituted monocyclic or bicyclic aryl or heteroaryl grouping defined below in which $R^3$ represents hydrogen, fluorine or chlorine, $R^4$ represents hydrogen, fluorine or chlorine, $R^5$ represents cyano, thiocarbamoyl, chlorine, bromine, methyl, trifluoromethyl, methoxy, difluoromethoxy or trifluoromethoxy, $R^6$ represents the following grouping

—$A^1$—$A^2$—$A^3$ in which $A^1$ represents a single bond, or represents oxygen, sulfur, —SO—, —$SO_2$—, —CO— or the grouping —N—$A^4$—, in which $A^4$ represents hydrogen, hydroxyl, methyl, ethyl, n- or i-propyl, methoxy, ethoxy, n- or i-propoxy, methylsulfonyl or ethylsulfonyl, $A^1$ furthermore represents methylene, ethane-1,1-diyl, ethane-1,2-diyl, propane-1,1-diyl, propane-1,2-diyl, propane-1,3-diyl, ethene-1,2,-diyl, propene-1,2-diyl, propene-1,3-diyl, ethine-1,2-diyl, propine-1,2-diyl or propine-1,3-diyl, $A^2$ represents a single bond, or represents oxygen, sulfur, —SO—, —$SO_2$—, —CO— or the grouping —N—$A^4$—, in which $A^4$ represents oxygen, hydroxyl, methyl, ethyl, n- or i-propyl, methoxy, ethoxy, n- or i-propoxy, methylsulfonyl, ethylsulfonyl, n- or i-propylsulfonyl or phenylsulfonyl, $A^2$ furthermore represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^3$ represents hydrogen, with the proviso that in this case $A^1$ and/or $A^2$ do(es) not represent a single bond, $A^3$ furthermore represents hydroxyl, amino, cyano, nitro, carboxyl, carbamoyl, sulfo, fluorine, chlorine or bromine, $A^3$ furthermore represents methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulfinyl, ethylsulfinyl, n- or i-propylsulfinyl, methylsulfonyl, ethylsulfonyl, n- or i-propylsulfonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, in each case optionally substituted by fluorine, chlorine, methoxy or ethoxy, $A^3$ furthermore represents propenyl, butenyl, propenyloxy, butenyloxy, propenylamino, butenylamino, propylidenamino, butylidenamino, propenyloxycarbonyl, butenyloxycarbonyl, propinyl, butinyl, propinyloxy, butinyloxy, propinylamino, butinylamino, propinyloxycarbonyl or butinyloxycarbonyl, in each case optionally substituted by fluorine or chlorine, $A^3$ furthermore represents cyclopropyl, cyclobutyl, cyclopentyl, cyclohexyl, cyclopropyloxy, cyclobutyloxy, cylopentyloxy, cyclohexyloxy, cyclopropylmethyl, cyclobutylmethyl, cyclopentylmethyl, cyclohexylmethyl, cyclopropylmethoxy, cyclo-butylmethoxy, cyclopentylmethoxy, cyclohexylmethoxy, cyclopentylidenamino, cyclohexylidenamino, cyclopentyloxy-carbonyl, cyclohexyloxycarbonyl, cyclopentylmethoxycarbonyl or cyclohexylmethoxycarbonyl, in each case optionally substituted by fluorine, chlorine, cyano, carboxyl, methyl, ethyl, n- or i-propyl, methoxycarbonyl or ethoxycarbonyl, $A^3$ furthermore represents phenyl, phenyloxy, benzyl, phenylethyl, benzyloxy, phenyloxycarbonyl or benzyloxycarbonyl, in each case optionally substituted by nitro, cyano, carboxyl, fluorine, chlorine, bromine, methyl, ethyl, n- or i-propyl, trifluoromethyl, methoxy, ethoxy, n- or i-propoxy, difluoromethoxy, trifluoromethoxy, methoxycarbonyl and/or ethoxycarbonyl, $A^3$ furthermore represents in each case optionally completely or partly hydrogenated pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolylmethyl, thiazolylmethyl, pyridinylmethyl, pyrimidinylmethyl, pyrazolylmethoxy, furylmethoxy or pyridylmethoxy, $R^7$ represents hydrogen, fluorine or chlorine, or in each case two adjacent radicals—$R^3$ and $R^4$, $R^4$ and $R^5$, $R^5$ and $R^6$ or $R^6$ and $R^7$—together represent one of the following groupings —Q³—CQ⁴—, —Q³—CQ⁴—Q⁵—, —Q³—C(R⁸, R⁹)—Q⁵—, —C(R⁸,R⁹)—CQ⁴—, —C(R⁸,R⁹)—Q³—CQ⁴—, —Q³—C(R⁸,R⁹)—C(R⁸,R⁹)—, —Q³—C(R⁸,R⁹)—C(R⁸,R⁹)—Q⁵—, —C(R⁸,R⁹)—C(R⁸,R⁹)—CQ⁴—, —Q³—C(R⁸)=C(R⁸)—, —C(R⁸)=C(R⁸)—CQ⁴—, —Q³C(R⁸,R⁹)—CQ⁴—, —N(R¹⁰)—C(R⁸,R⁹)—CQ⁴—, —C(R⁸)=N—, —Q³—CQ⁴—C(R⁸,R⁹)—, —Q³—CQ⁴—N(R¹⁰)—, —Q³—C(R⁸,R⁹)—CQ⁴—N(R¹⁰)—, —C(R⁸,R⁹)—Q³—CQ⁴—N(R¹⁰)—, —C(R⁸,R⁹)—C(R⁸,R⁹)—N(R¹⁰)—, —C(R⁸,R⁹)—C(R⁸,R⁹)—CQ⁴—N(R¹⁰)—, —C(R⁸)=C(R⁸)—N(R¹⁰—, —C(R⁸)=C(R⁸)—CQ⁴—N(R¹⁰)—, —C(R⁸,R⁹)—CQ⁴—N(R¹⁰)—, —N(R¹⁰)—C(R⁸,R⁹)—CQ⁴—N(R¹⁰)—, —C(R⁸)=N—N(R¹⁰)—, —Q³—CQ⁴—C(R⁸,R⁹)—N(R¹⁰)—, Q³—C(R⁸,R⁹)—C(R⁸,R⁹)—CQ⁴—N(R¹⁰)—, in which Q³, Q⁴ and Q⁵ are identical or different and in each case represent oxygen or sulfur, R⁸ and R⁹ are identical or different and individually represent hydrogen, fluorine, chlorine, methyl or ethyl, or together represent ethane-1,2-diyl (dimethylene), and R¹⁰ represents hydrogen or hydroxyl, or represents methyl, ethyl, n- or i-propyl or n-, i-, s- or t-butyl which are optionally substituted by cyano, fluorine, chlorine, methoxy, ethoxy, acetyl, propionyl, methoxycarbonyl or ethoxycarbonyl, R¹⁰ furthermore represents propenyl, butenyl, propinyl or butinyl, in each case optionally substituted by fluorine, chlorine or bromine, R¹⁰ furthermore represents cyclopropyl, cyclobutyl, cyclopentyl, cyclohexyl, cyclopropylmethyl, cyclobutylmethyl, cyclopentylmethyl or cyclohexylmethyl, in each case optionally substituted by fluorine, chlorine, bromine, methyl or ethyl, R¹⁰ furthermore represents methoxy, ethoxy, n- or i-propoxy, n-, i- or s-butoxy, propenyloxy or butenyloxy, in each case optionally substituted by fluorine and/or chlorine, and R¹⁰ furthermore represents benzyl or benzyloxy, in each case optionally substituted by cyano, fluorine, chlorine, methyl, ethyl, trifluoromethyl, methoxy, ethoxy, difluoromethyl or trifluoromethoxy, the already known compounds 4-(3,-dichloro-phenyl)-1,2-dimethyl-5-thioxo-1,2,4-triazolidin-3-one and 4-(4-chloro-3-trifluoromethyl-phenyl)-1,2-dimethyl-5-thioxo-1,2,4-triazolidin-3-one (cf. DE 2952685 and DE 3026739) being excluded by disclaimer.

The abovementioned definitions of radicals given generally or in preferred ranges apply both to the end products of the formula (I) and also correspondingly to the starting substances or intermediate products in each case required for the preparation. These definitions of radicals can be combined with one another as desired, that is to say also between the stated ranges of preferred compounds.

Examples of the compounds of the formula (I) according to the invention are given in the following groups.

Group 1

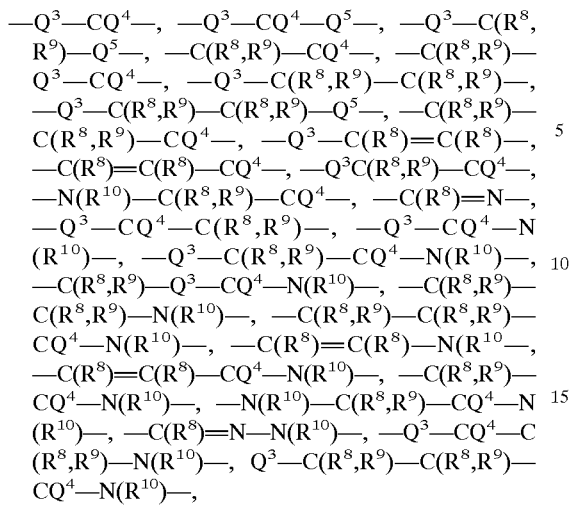

(IA-1)

Ar here has, for example, the meanings listed below:

2,4-dichloro-phenyl, 3-chloro-4-fluoro-phenyl, 2-chloro-4-cyano-phenyl, 2-fluoro-4-cyano-phenyl, 4,5-difluoro-phenyl, 2,4,5-trichloro-phenyl, 2,4-dichloro-5-fluoro-phenyl, 2-chloro-4,5-difluoro-phenyl, 4-chloro-2,5-di-fluoro-phenyl, 5-chloro-2,4-difluoro-phenyl, 2-fluoro-5-chloro-4-cyano-phenyl, 2,4,5-trifluoro-phenyl, 2,5-dichloro-4-cyano-phenyl, 2-chloro-5-fluoro-4-cyano-phenyl, 2-chloro-4,5-dicyano-phenyl, 2-chloro-4-fluoro-5-cyano-phenyl, 2,5-difluoro-4-cyano-phenyl, 4-cyano-3-methyl-phenyl, 2-chloro-4-cyano-5-methyl-phenyl, 2,4-dichloro-5-methoxy-phenyl, 2,4-dichloro-5-ethoxy-phenyl, 2,4-dichloro-5-n-propoxy-phenyl, 2,4-dichloro-5-i-propoxy-phenyl, 4-chloro-2-fluoro-5-methoxy-phenyl, 4-chloro-2-fluoro-5-ethoxy-phenyl, 4-chloro-2-fluoro-5-n-propoxy-phenyl, 4-chloro-2-fluoro-5-i-propoxy-phenyl, 2-fluoro-4-cyano-5-methyl-phenyl, 2,4-dichloro-5-methyl-phenyl, 2-chloro-4-cyano-5-trifluoromethyl-phenyl, 4-fluoro-3-trifluoromethyl-phenyl, 2-fluoro-4-cyano-5-trifluoromethyl-phenyl, 2-chloro-4-methyl-5-trifluoromethyl-phenyl, 2-chloro-5-fluoro-4-methoxy-phenyl, 2-fluoro-4-methoxy-5-methyl-phenyl, 2,5-difluoro-4-thicarbamoyl-phenyl, 2-chloro-4-fluoro-5-i-propoxy-phenyl, 2-fluoro-4-cyano-5-methoxy-phenyl, 2-fluoro-4-cyano-5-i-propoxy-phenyl, 2-chloro-4-cyano-5-(2-propinyloxy)-phenyl, 2-fluoro-4-cyano-5-(1-methyl-2-propinyloxy)-phenyl, 2-fluoro-4-chloro-5 (1-methyl-2-propinyloxy)-phenyl, 2-chloro-4-thiocarbamoyl-5-i-propoxy-phenyl, 2-fluoro-4-cyano-5-(2-propenyloxy)-phenyl, 2-fluoro-4-chloro-5-(2-propenyloxy)-phenyl, 2-chloro-4-cyano-5-methylsulfonylamino-phenyl, 2-fluoro-4-cyano-5-ethylsulfonylamino-phenyl, 2-fluoro-4-thiocarbamoyl-5-methylsulfonylamino-phenyl, 2-chloro-4-cyano-5-ethylsulfonylamino-phenyl, 2-fluoro-4-cyano-5-cyclopropylsulfonylamino-phenyl, 2-fluoro-4-cyano-5-i-propylsulfonylamino-phenyl, 2-chloro-4-thiocarbamoyl-5-ethylsulfonylamino-phenyl, 2-chloro-4-cyano-5-cyanamino-phenyl, 2-fluoro-4-cyano-5-(2,2-difluoroethylsulfonylamino)-phenyl, 2-fluoro-4-cyano-5-phenyl-sulfonylamino-phenyl, 2-fluoro-4-cyano-5-t-butylsulfonyla-mino-phenyl, 2-chloro-4-cyano-5-methoxycarbonyl-phenyl, 2-fluoro-4-cyano-5-ethoxycarbonyl-phenyl, 2-fluoro-4-chloro-5-ethoxycarbonyl-phenyl, 2-fluoro-4-thiocarbamoyl-5-methoxy-carbonyl-phenyl, 2-chloro-4-cyano-5-(N-cyclopropyl-ethylsulfonylamino)-phenyl, 2-fluoro-4-cyano-5-(1-methyl-2-propinylthio)-phenyl, 2-fluoro-4-cyano-5-methylamino-phenyl, 2-chloro-4-thiocarbamoyl-5-methoxycarbonylmethyl-phenyl, 2-chloro-4-cyano-5-(N-methyl-ethylsulfonylamino)-phenyl, 2-fluoro-4-cyano-5-i-propoxycarbonyl-phenyl, 2-fluoro-4-chloro-5-i-propoxycarbonyl-phenyl, 2-fluoro-4-cyano-5-(bis-ethylsulfonyl-amino)-phenyl, 2-fluoro-4-cyano-5-(N-methylsulfonylethylsulfonylamino)-phenyl, 2-fluoro-4-cyano-5(1-methoxycarbonyl-ethoxy)-phenyl, 2-fluoro-4-cyano-5(1-ethoxycarbonyl-ethoxy)-phenyl, 2-fluoro-4-chloro-5(1-methoxycarbonyl-ethoxy)-phenyl, 2-fluoro-4-chloro-5-(1-ethoxycarbonyl-ethoxy)-phenyl, 2-fluoro-4-cyano-5-cyclopropyloxy-phenyl, 2-chloro-4-cyano-5-dimethylamino-phenyl, 2-fluoro-4-cyano-5-tetrahydrofurylmethoxy-phenyl, 4-chloro-2-fluoro-5-tetrahydrofurylmethoxy-phenyl, 2-fluoro-4-cyano-5-amino-phenyl, 2-fluoro-4-cyano-5-methylaminocarbonyl-phenyl, 2-fluoro-4-cyano-5-methylsulfonyloxy-phenyl, 2-chloro-4-cyano-5-difluoromethoxy-phenyl, 2-fluoro-4-chloro-5-methoxycarbonylmethoxy-phenyl, 2-fluoro-4-chloro-5-ethoxycarbonyl-methoxy-phenyl, 2-fluoro-4-cyano-5-methoxycarbonylmethoxy-phenyl, 2-fluoro-4-cyano-5-ethoxycarbonylmethoxy-phenyl, 4-cyano-3-(1-methyl-2-propinyloxy)-phenyl, 2-fluoro-4-cyano-5-dimethyl-aminocarbonyl-phenyl, 2-fluoro-4-cyano-5-cyanomethoxy-phenyl, 2-fluoro-4-cyano-5-(2-chloro-2-propenyloxy)-phenyl, 2-fluoro-4-cyano-5-hydroxy-phenyl, 2-fluoro-4-cyano-5-nitro-phenyl, 2-fluoro-4-cyano-5-diethoxyphosphorylamino-phenyl, 2-fluoro-4-cyano-5-chlorosulfonyl-phenyl, 2-fluoro-4-cyano-5-formylamino-phenyl, 2-chloro-4-cyano-5-ethoxycarbonyloxy-phenyl, 2-fluoro-4-cyano-5-diethoxyphosphorylmethoxy-phenyl, 4-chloro-2-fluoro-5-diethoxy-phosphorylmethoxy-phenyl, 2-fluoro-4-cyano-5-(1-diethoxyphosphoryl-ethoxy)-phenyl, 4-chloro-2-fluoro-5-(1-diethoxyphosphoryl-ethoxy)-phenyl-2-chloro-4-cyano-5-hydroxy-phenyl, 2-fluoro-4-cyano-5-(N,N-diacetyl-amino)-phenyl, 2-fluoro-4-cyano-5-acetylamino-phenyl, 2-chloro-4-cyano-5-thiocyanato-phenyl, 2-fluoro-4-cyano-5-diethylaminooxy-phenyl, 2-fluoro-4-cyano-5-tetrahydrofuryloxy-phenyl, 2-fluoro-4-cyano-5-ureido-phenyl, 2-fluoro-4-cyano-5-dimethoxymethylenamino-phenyl, 2-chloro-4-cyano-5-ethoxymethylenamino-phenyl, 2-fluoro-4-cyano-5-(2-chloro-ethoxycarbonyloxy)-phenyl, 2-chloro-4-cyano-5-dimethylaminomethylenamino-phenyl, 2-chloro-4-cyano-5-perhydropyran-4-yloxy)-phenyl, 2-fluoro-4-cyano-5-(2-methoxycarbonyl-ethyl)-phenyl, 4-chloro-2-fluoro-5-(2-methoxycarbonyl-ethyl)-phenyl, 2-chloro-4-cyano-5-(2-carboxy-2-chloro-ethyl)phenyl, 2-fluoro-4-cyano-5-(2-chloro-2-methoxycarbonyl-ethyl)-phenyl, 2-fluoro-4-chloro-5-(2-chloro-2-methoxycarbonyl-ethyl)-phenyl, 2-fluoro-4-cyano-5-(2-chloro-2-ethoxycarbonyl-ethyl)-phenyl, 2-fluoro-4-chloro-5-(2-chloro-2-ethoxycarbonyl-ethyl)-phenyl, 2-fluoro-4-cyano-5-(2-bromo-2-methoxycarbonyl-ethyl)-phenyl, 2-fluoro-4-chloro-5-(2-bromo-2-methoxycarbonyl-ethyl)phenyl, 2-fluoro-4-cyano-5-(2-bromo-2-ethoxycarbonyl-ethyl)-phenyl, 2-fluoro-4-chloro-5-(2-bromo-2-ethoxycarbonyl-ethyl)-phenyl, 2-fluoro-4-cyano-5-(2,3-dibromo-2-methoxycarbonyl-ethyl)-phenyl, 2-fluoro-4-chloro-5-(2,3-dibromo-2-methoxycarbonyl-ethyl)-phenyl, 2-fluoro-4-cyano-5-(2,3-dibromo-2-ethoxycarbonyl-ethyl)-phenyl, 2-fluoro-4-chloro-5-(2,3-dibromo-2-ethoxycarbonyl-ethyl)-phenyl, 2-fluoro-4-cyano-5-(2-chloro-2-s-butoxycarbonyl)phenyl, 2-fluoro-4-cyano-5-(2-chloro-2-carbamoyl-ethyl)-phenyl, 2-fluoro-4-cyano-5-(2-chloro-2-methoxycarbonyl-1-methyl-ethyl)-phenyl, 2-fluoro-4-cyano-5-(1,2-dibromo-2-methoxycarbonyl-ethyl)-phenyl, 2-chloro-4-cyano-5-(2-chloro-2-i-propoxy-carbonyl-ethyl)-phenyl, 2,4-dichloro-5-(2-methoxycarbonyl-ethyl)-phenyl, 2-fluoro-4-cyano-5-(2-carboxy-2-chloro-ethyl)-phenyl, 2-fluoro-4-cyano-5-(2-chloro-2-ethylamino-carbonyl-ethyl)-phenyl, 2-fluoro-4-cyano-5-(2-allylaminocarbonyl-2-chloro-ethyl)-phenyl, 2-fluoro-4-cyano-5-(2-methoxycarbonyl-ethenyl)-phenyl, 2-fluoro-4-chloro-5-(2-methoxycarbonyl-ethenyl)-phenyl, 2-fluoro-4-cyano-5-(2-ethoxycarbonyl-ethenyl)-phenyl, 2-fluoro-4-chloro-5-(2-ethoxycarbonyl-ethenyl)-phenyl, 2-fluoro-4-cyano-5-(2-chloro-2-methylaminocarbonyl-ethyl)-phenyl, 2-fluoro-4-cyano-5-(2-chloro-2-ethylaminocarbonyl-ethyl)-phenyl, 2-fluoro-4-cyano-5-(2-chloro-2-cyclopropylamino-carbonyl-ethyl)-phenyl, 2-fluoro-4-chloro-5-(2-chloro-2-methylaminocarbonyl-ethyl)-phenyl, 2-fluoro-4-chloro-5-(2-chloro-2-ethylaminocarbonyl-ethyl)-phenyl, 2-fluoro-4-chloro-5-(2-chloro-2-cyclopropylaminocarbonyl-ethyl)-phenyl, 2-fluoro-4-cyano-5-(2-chloro-2-dimethylaminocarbonyl-ethyl)-phenyl, 2-fluoro-4-cyano-5-(2-chloro-2-ethylsulfonylaminocarbonyl-ethyl)-phenyl, 2-fluoro-4-chloro-5-(2-chloro-2-ethylsulfonylaminocarbonyl-ethyl)-phenyl, 2-fluoro-4-chloro-5-(2-carboxy-ethenyl)-phenyl, 2-fluoro-4-thiocarbamoyl-5-(2-ethylaminocarbonyl-ethenyl)-phenyl, 2,6-difluoro-4-cyano-5-i-propoxy-phenyl, 2-chloro-4-cyano-6-fluoro-3-i-propoxy-phenyl, 2-chloro-6-fluoro-3-i-propoxy-4-trifluoromethyl-phenyl, 2,6-di-chloro-4-cyano-3-fluoro-phenyl, 2-fluoro-4-cyano-5-(1-ethoxycarbonyl-ethyl)phenyl, 2-chloro-4-cyano-5-(1-ethoxycarbonyl-ethyl)-phenyl, 2-chloro-4-cyano-5-carboxy-phenyl, 2-fluoro-4-chloro-5-(1-ethoxycarbonyl-ethyl)-phenyl, 2-fluoro-4-chloro-5-(1-i-propoxycarbonyl-ethyl)-phenyl, 2-fluoro-4-cyano-5-i-butoxy-phenyl), 2-chloro-4-cyano-5-i-butoxy-phenyl, 2-chloro-4-cyano-5-(2-methoxy-ethoxy)-phenyl, 2-fluoro-4-chloro-5(2-methoxy-ethoxy)-phenyl, 2-fluoro-4-chloro-5-i-butoxy-phenyl, 4-hydroxy-4-ethoxycarbonyl-phenyl, 2-fluoro-4-cyano-5-i-propoxycarbonyl-phenyl, 2-fluoro-4-hydroxy-5-i-propoxycarbonyl-phenyl, 2-fluoro-4-cyano-5-(2-oxetanyloxy)-phenyl, 2-fluoro-4-cyano-5-(2-oxetanyloxy-carbonylmethoxy)-phenyl, 2-fluoro-4-cyano-5-(2-oxetanyloxy)-phenyl, 2-fluoro-4-cyano-5-(2-chloro-2-propenyloxy)-phenyl, 4-chloro-2-fluoro-5-(2-chloro-2-propenyloxy)-phenyl, 2-fluoro-4-chloro-5-methoxycarbonylmethylthio-phenyl, 2-fluoro-4-chloro-5-ethoxycarbonylmethylthio-phenyl, 2-fluoro-4-cyano-5-methoxycarbonylmethylthio-phenyl, 2-fluoro-4-cyano-5-ethoxycarbonylmethylthio-phenyl, 2-fluoro-4-chloro-5-(1-methoxycarbonyl-ethylthio)-phenyl, 2-fluoro-4-chloro-5(1-ethoxycarbonyl-ethylthio)-phenyl, 2-fluoro-4-cyano-5-(1-methoxycarbonyl-ethylthio)-phenyl, 2-fluoro-4-cyano-5-(1-ethoxycarbonyl-ethylthio)-phenyl,

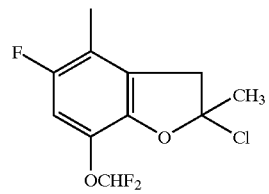
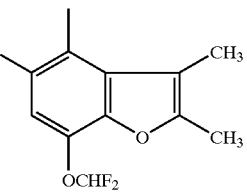

-continued
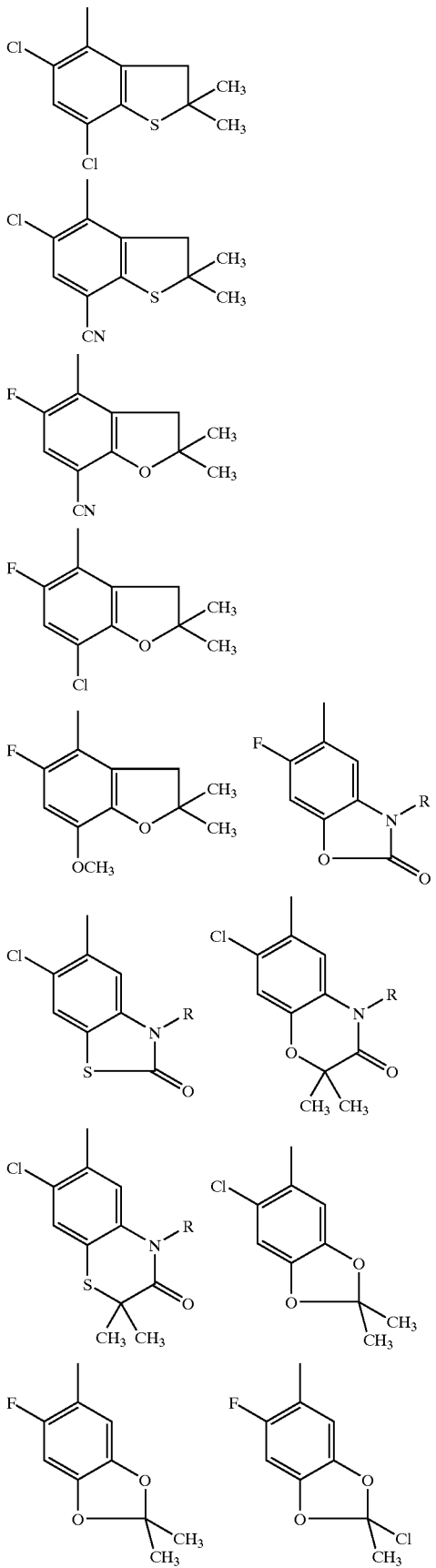
-continued
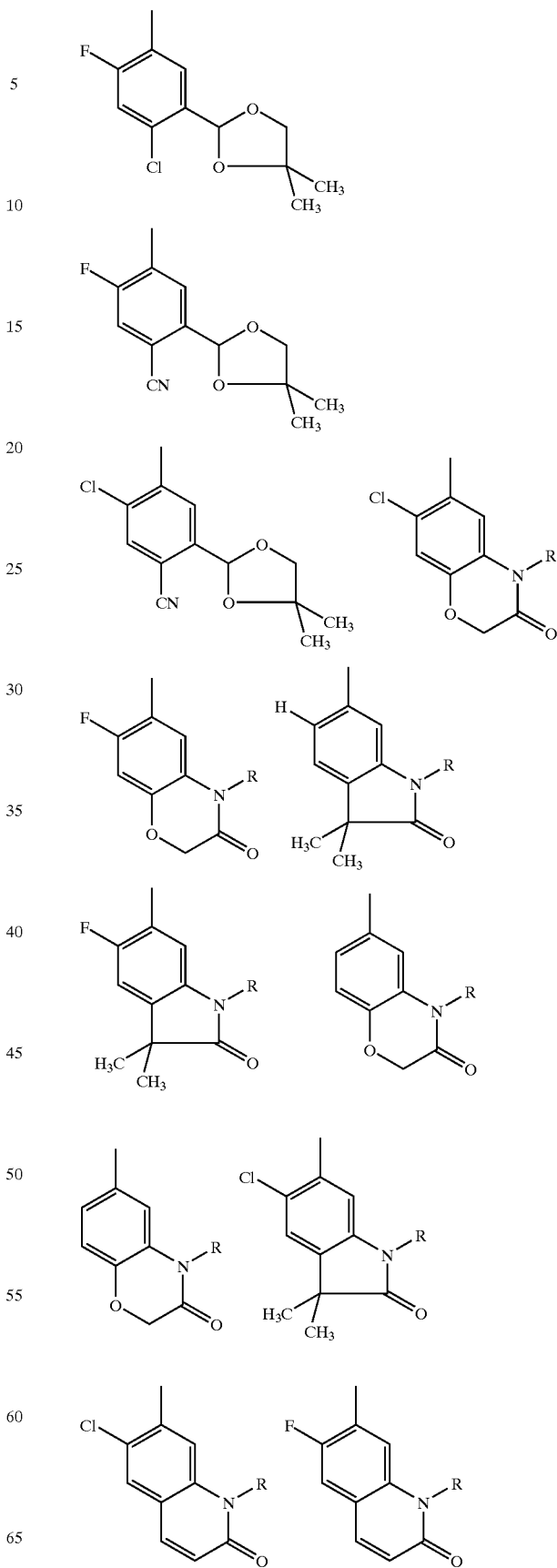

-continued

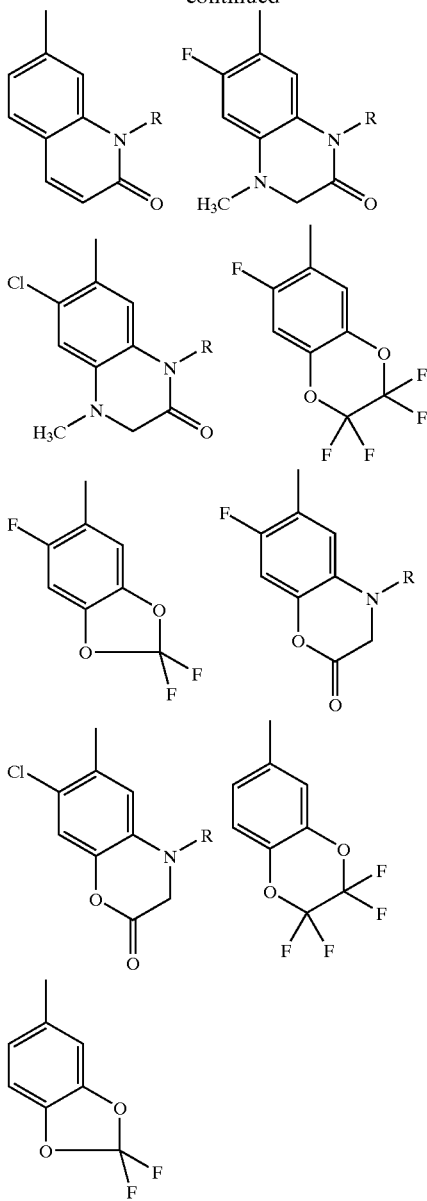

R here represents, for example, hydrogen, hydroxyl, methyl, ethyl, n- or i-propyl, i- or s-butyl, allyl, propargyl, methoxy, ethoxy, n- or i-propoxy, cyanomethyl, carboxymethyl, methoxymethyl, ethoxymethyl, methoxycarbonylmethyl, ethoxycarbonylmethyl, acetyl, propionyl, methoxycarbonyl, ethoxycarbonyl, methylsulfonyl or ethylsulfonyl.

Group 2

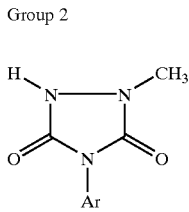
(IA-2)

Ar here has, for example, the meanings listed above in Group 1.

Group 3

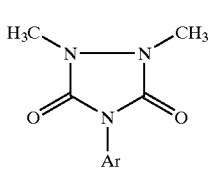
(IA-3)

Ar here has, for example, the meanings listed above in Group 1.

Group 4

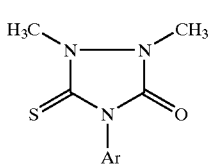
(IA-4)

Ar here has, for example, the meanings listed above in Group 1.

Group 5

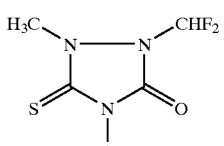
(IA-5)

Ar here has, for example, the meanings listed above in Group 1.

Group 6

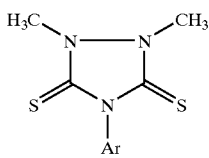
(IA-6)

Ar here has, for example, the meanings listed above in Group 1.

Group 7

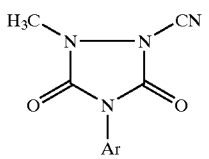
(IA-7)

Group 8

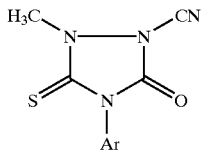
(IA-8)

Ar here has, for example, the meanings listed above in Group 1.

Group 9

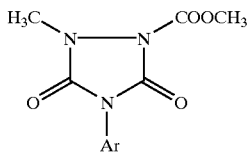
(IA-9)

Ar here has, for example, the meanings listed above in Group 1.

Group 10

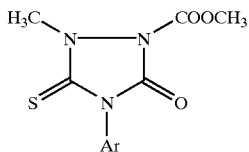
(IA-10)

Ar here has, for example, the meanings listed above in Group 1.

Group 11

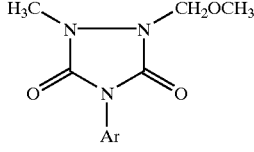
(IA-11)

Ar here has, for example, the meanings listed above in Group 1.

Group 12

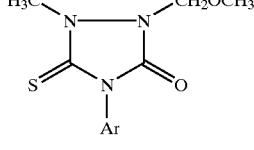
(IA-12)

Ar here has, for example, the meanings listed above in Group 1.

Group 13

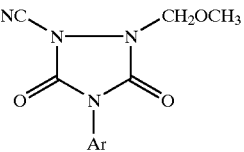
(IA-13)

Ar here has, for example, the meanings listed above in Group 1.

Group 14

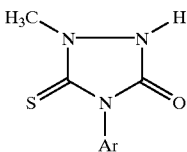
(IA-14)

Ar here has, for example, the meanings listed above in Group 1.

Group 15

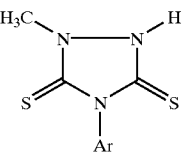
(IA-15)

Ar here has, for example, the meanings listed above in Group 1.

Group 16

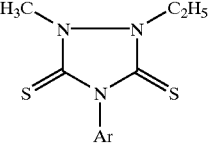
(IA-16)

Ar here has, for example, the meanings listed above in Group 1.

Group 17

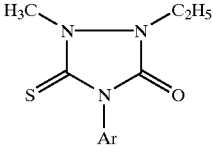
(IA-17)

Ar here has, for example, the meanings listed above in Group 1.

Group 18

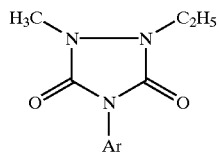
(IA-18)

Ar here has, for example, the meanings listed above in Group 1.

Group 19

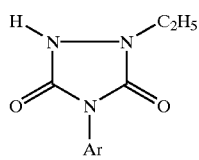
(IA-19)

Ar here has, for example, the meanings listed above in Group 1.

Group 20

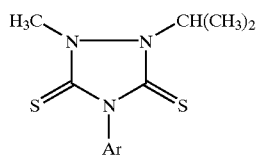
(IA-20)

Ar here has, for example, the meanings listed above in Group 1.

Group 21

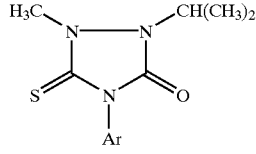
(IA-21)

Ar here has, for example, the meanings listed above in Group 1.

Group 22

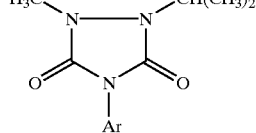
(IA-22)

Ar here has, for example, the meanings listed above in Group 1.

Group 23

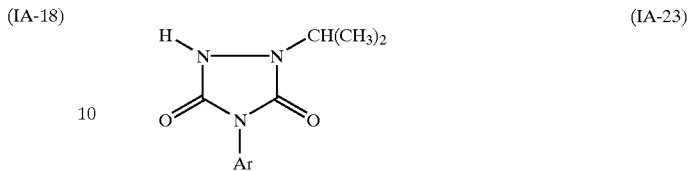
(IA-23)

Ar here has, for example, the meanings listed above in Group 1.

Group 24

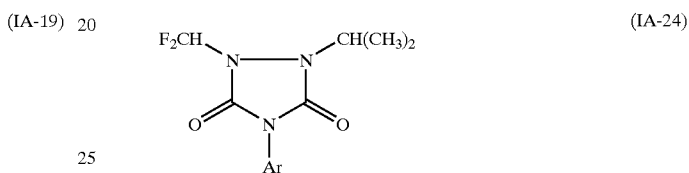
(IA-24)

Ar here has, for example, the meanings listed above in Group 1.

Group 25

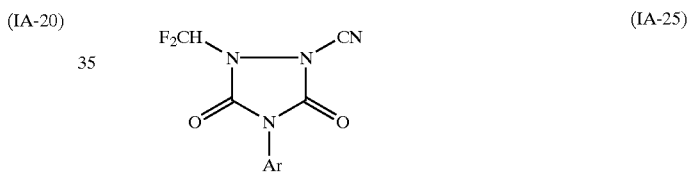
(IA-25)

Ar here has, for example, the meanings listed above in Group 1.

Group 26

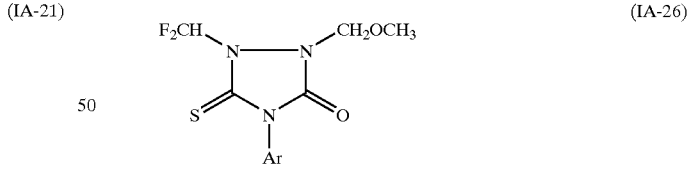
(IA-26)

Ar here has, for example, the meanings listed above in Group 1.

Group 27

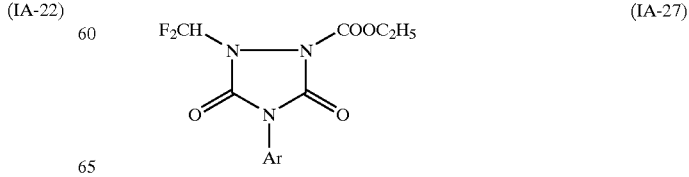
(IA-27)

Ar here has, for example, the meanings listed above in Group 1.

Group 28

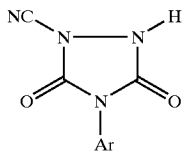
(IA-28)

Ar here has, for example, the meanings listed above in Group 1.

Group 29

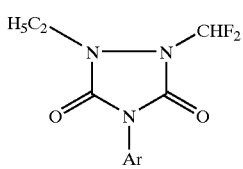
(IA-29)

Ar here has, for example, the meanings listed above in Group 1.

Group 30

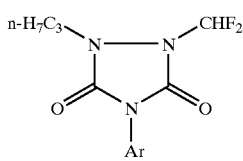
(IA-30)

Ar here has, for example, the meanings listed above in Group 1.

Group 31

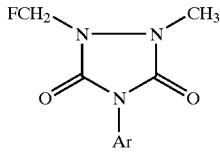
(IA-31)

Ar here has, for example, the meanings listed above in Group 1.

Group 32

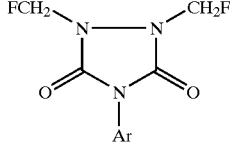
(IA-32)

Ar here has, for example, the meanings listed above in Group 1.

Group 33

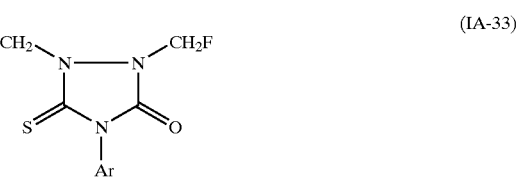
(IA-33)

Ar here has, for example, the meanings listed above in Group 1.

Group 34

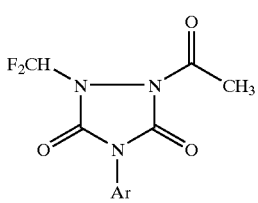
(IA-34)

Ar here has, for example, the meanings listed above in Group 1.

Group 35

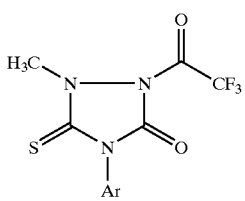
(IA-35)

Ar here has, for example, the meanings listed above in Group 1.

Group 36

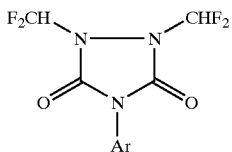
(IA-36)

Ar here has, for example, the meanings listed above in Group 1.

Group 37

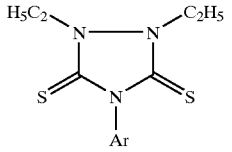
(IA-37)

Ar here has, for example, the meanings listed above in Group 1.

Group 38

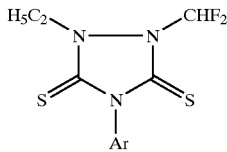
(IA-38)

Ar here has, for example, the meanings listed above in Group 1.

Group 39

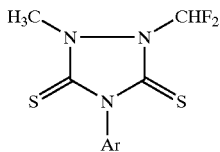
(IA-39)

Ar here has, for example, the meanings listed above in Group 1.

Group 40

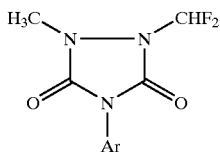
(IA-40)

Ar here has, for example, the meanings listed above in Group 1.

Group 41

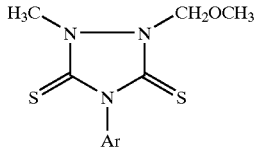
(IA-41)

Ar here has, for example, the meanings listed above in Group 1.

Group 42

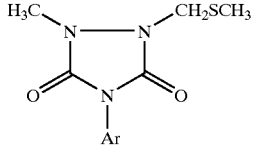
(IA-42)

Ar here has, for example, the meanings listed above in Group 1.

Group 43

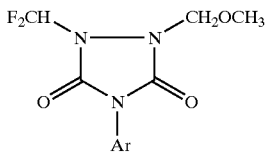
(IA-43)

Ar here has, for example, the meanings listed above in Group 1.

Group 44

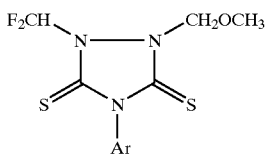
(IA-44)

Ar here has, for example, the meanings listed above in Group 1.

Group 45

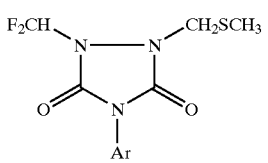
(IA-45)

Ar here has, for example, the meanings listed above in Group 1.

Group 46

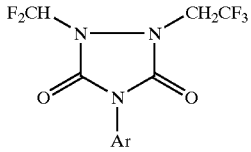
(IA-46)

Ar here has, for example, the meanings listed above in Group 1.

Group 47

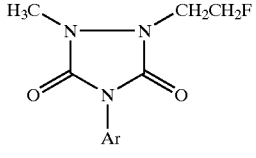
(IA-47)

Ar here has, for example, the meanings listed above in Group 1.

Group 48

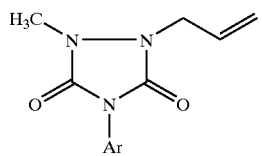
(IA-48)

Ar here has, for example, the meanings listed above in Group 1.

Group 49

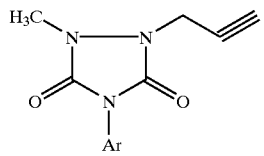
(IA-49)

Ar here has, for example, the meanings listed above in Group 1.

Group 50

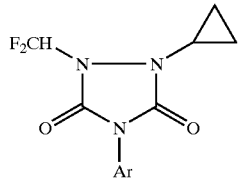
(IA-50)

Ar here has, for example, the meanings listed above in Group 1.

Group 51

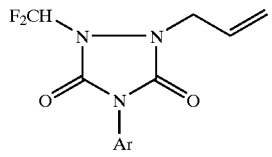
(IA-51)

Ar here has, for example, the meanings listed above in Group 1.

Group 52

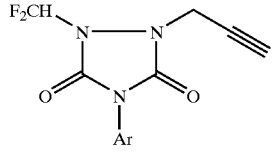
(IA-52)

Ar here has, for example, the meanings listed above in Group 1.

Group 53

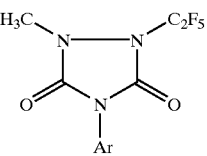
(IA-53)

Ar here has, for example, the meanings listed above in Group 1.

Group 54

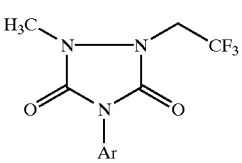
(IA-54)

Ar here has, for example, the meanings listed above in Group 1.

Group 55

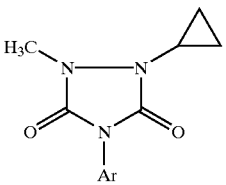
(IA-55)

Ar here has, for example, the meanings listed above in Group 1.

Group 56

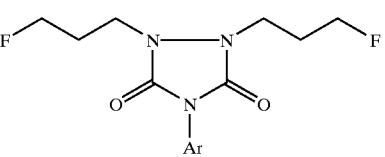
(IA-56)

Ar here has, for example, the meanings listed above in Group 1.

Group 57

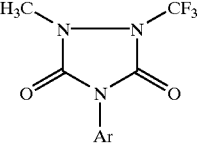
(IA-57)

Ar here has, for example, the meanings listed above in Group 1.

Group 58

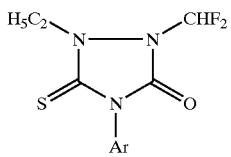

(IA-58)

Ar here has, for example, the meanings listed above in Group 1.

Group 59

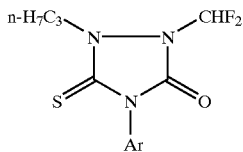

(IA-59)

Ar here has, for example, the meanings listed above in Group 1.

Group 60

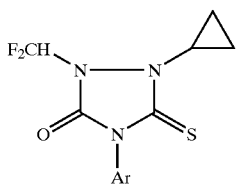

(IA-60)

Ar here has, for example, the meanings listed above in Group 1.

Group 61

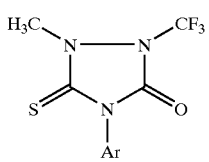

(IA-61)

Ar here has, for example, the meanings listed above in Group 1.

Group 62

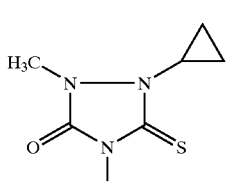

(IA-62)

Ar here has, for example, the meanings listed above in Group 1.

Group 63

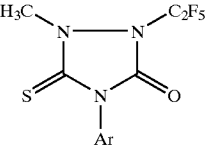

(IA-63)

Ar here has, for example, the meanings listed above in Group 1.

Group 64

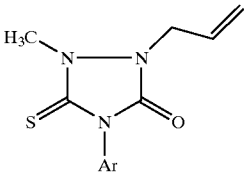

(IA-64)

Ar here has, for example, the meanings listed above in Group 1.

Group 65

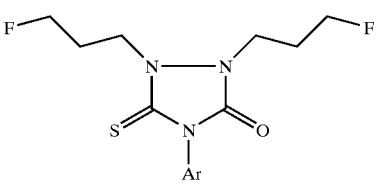

(IA-65)

Ar here has, for example, the meanings listed above in Group 1.

Group 66

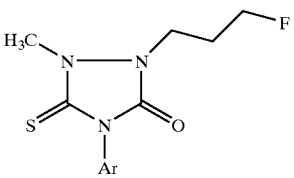

(IA-66)

Ar here has, for example, the meanings listed above in Group 1.

Group 67

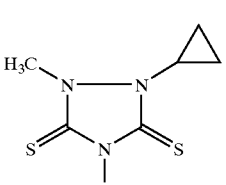

(IA-67)

Ar here has, for example, the meanings listed above in Group 1.

Group 68

(IA-68)

Ar here has, for example, the meanings listed above in Group 1.

Group 69

(IA-69)

Ar here has, for example, the meanings listed above in Group 1.

Group 70

(IA-70)

Ar here has, for example, the meanings listed above in Group 1.

Group 71

(IA-71)

Ar here has, for example, the meanings listed above in Group 1.

Group 72

(IA-72)

Ar here has, for example, the meanings listed above in Group 1.

Group 73

(IA-73)

Ar here has, for example, the meanings listed above in Group 1.

Group 74

(IA-74)

Ar here has, for example, the meanings listed above in Group 1.

Group 75

(IA-75)

Ar here has, for example, the meanings listed above in Group 1.

If, for example, 4(4-cyano-2,5-difluoro-phenyl)-1-methoxycarbonylthiosemicarbazide is used as the starting substance, the course of the reaction in process (a) according to the invention can be represented by the following equation:

If, for example, 2-(4-chloro-2-fluoro-5-methoxy-phenylimino)-3,4-dimethyl-3,4-dihydro-5-oxo-1,3,4-thiadiazole is used as the starting substance, the course of the reaction in process (b) according to the invention can be outlined by the following equation:

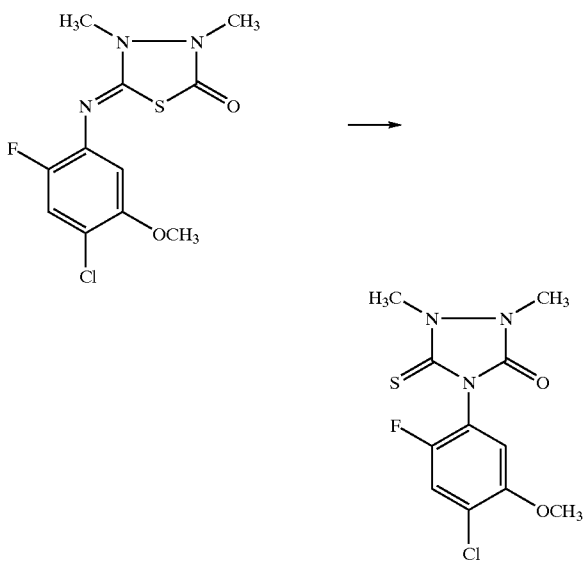

Formula (II) provides a general definition of the (thio)semicarbazide derivatives to be used as starting substances in process (a) according to the invention for the preparation of the compounds of the general formula (I). In formula (II), $Q^1$, $Q^2$, $R^1$, $R^2$ and Ar preferably or in particular have those meanings which have already been mentioned above as preferred or as particularly preferred for $Q^1$, $Q^2$, $R^1$, $R^2$ and Ar in connection with the description of the compounds of the formula (I); R preferably represents alkyl having 1–4 carbon atoms, in particular methyl or ethyl.

The starting substances of the formula (II) are known and/or can be prepared by known processes (cf. Synthesis 1982, 159–160; DE 1200824, DE 2952685 and DE 3026739).

The (thio)semicarbazide derivatives of the formula (II) are obtained when (α) aryl iso(thio)cyanates of the general formula (IV)

in which

Ar and $Q^1$ have the abovementioned meanings, are reacted with carbazates of the general formula (XI)

in which $Q^2$, $R^1$ and $R^2$ have the abovementioned meanings and

R represents alkyl, and preferably represents $C_1$–$C_6$-alkyl, and particularly preferably represents methyl or ethyl, if appropriate in the presence of a diluent, such as, for example, toluene, at temperatures of between 0° C. and 150° C. (cf. the preparation examples), or when (β) arylamines of the general formula (XII)

in which

Ar has the abovementioned meaning, are reacted with (thio)carbonyl-diimidazole of the formula (XIII)

in which $Q^1$ has the abovementioned meaning and

Im represents imidazolyl, and with carbazates of the general formula (XI)

in which $Q^2$, $R^1$ and $R^2$ have the abovementioned meanings and

R represents alkyl, and preferably represents $C_1$–$C_6$-alkyl, and particularly preferably represents methyl or ethyl, if appropriate in the presence of a reaction auxiliary, such as, for example, potassium hydroxide, and if appropriate in the presence of a diluent, such as, for example, methanol, ethanol and/or water, at temperatures of between 0° C. and 100° C.

The aryl iso(thio)cyanates of the formula (IV) required as precursors are known and/or can be prepared by known processes (cf. DE 4327743, DE 4335438 and DE 4343451).

The carbazates of the formula (VIII) furthermore required as precursors are known organic chemicals.

Process (a) according to the invention is preferably carried out in the presence of a suitable reaction auxiliary. Possible reaction auxiliaries are all the customary organic or inorganic bases. These include, for example, alkali metal or alkaline earth metal hydrides, hydroxides, amides, alcoholates, acetates, carbonates or hydrogencarbonates, such as, for example, lithium, sodium, potassium or calcium hydride, lithium, sodium or potassium amide, sodium or potassium methylate, sodium or potassium ethylate, sodium or potassium propylate, aluminum isopropylate, sodium or potassium tert-butylate, sodium or potassium hydroxide, ammonium hydroxide, sodium, potassium or calcium acetate, ammonium acetate, sodium, potassium, rubidium, cesium, magnesium or calcium carbonate, ammonium carbonate and sodium or potassium hydrogencarbonate, and basic organic nitrogen compounds, such as trimethylamine, triethylamine tripropylamine, tributylamine, ethyl-diisopropylamine, N,N-dimethylcyclohexylamine, dicyclohexylamine, ethyl-dicyclohexylamine, N,N-dimethylaniline, N,N-dimethyl-benzylamine, pyridine, 2-methyl-, 3-methyl- and 4-methyl-pyridine, 2,4-dimethyl-, 2,6-dimethyl-, 3,4-dimethyl- and 3,5-dimethyl-pyridine, 5-ethyl-2-methyl-pyridine, N-methylpiperidine, N,N-dimethylaminopyridine, diazabicyclooctane, (DABCO), diazabicyclononene (DBN) or diazabicycloundecene (DBU).

Possible diluents for carrying out process (a) according to the invention are the customary organic solvents. These include, in particular, aliphatic, alicyclic or aromatic, optionally halogenated hydrocarbons, such as, for example, pentane, hexane, heptane, petroleum ether, ligroin, benzine, benzene, toluene, xylene, chlorobenzene, dichlorobenzene, cyclohexane, methylcyclohexane, methylene chloride, chloroform or carbon tetrachloride; ethers, such as diethyl ether, diisopropyl ether, t-butyl methyl ether, t-pentyl methyl ether, dioxane, tetrahydro-furan, ethylene glycol dimethyl or diethyl ether or diethylene glycol dimethyl or diethyl ether; ketones, such as acetone, butanone or methyl isobutyl ketone; nitriles, such as acetonitrile, propionitrile, butyronitrile or benzonitrile; amides, such as N,N-dimethylformamide, N,N-dimethylacetamide, N-methylformanilide, N-methyl-pyrrolidone or hexamethylphosphoric acid triamide; esters, such as methyl, ethyl, n- or i-propyl or n-, i- or s-butyl acetate; sulfoxides, such as dimethyl sulfoxide; alcohols, such as methanol, ethanol, n- or i-propanol, n-, i-, s- or t-butanol, ethylene glycol monomethyl or monoethyl ether, diethylene glycol monomethyl ether or diethylene glycol monoethyl ether; and mixtures thereof with water or pure water.

The reaction temperatures can be varied within a substantial range when carrying out process (a) according to the invention. The process is in general carried out at temperatures of between 0° C. and +150° C., preferably at temperatures between 10° C. and 120° C.

Process (a) according to the invention is in general carried out under normal pressure. However, it is also possible to carry out the process under increased or reduced pressure—in general between 0.1 bar and 10 bar.

For carrying out process (a) according to the invention, the starting substances of formula (II) are in general initially introduced into the reaction vessel in a suitable diluent and—if appropriate after addition of a reaction auxiliary—are stirred at the required temperature until the reaction has ended. Working up can be carried out in the customary manner (cf. the preparation examples).

Formula (III) provides a general definition of the aryliminoheterocyclic compounds to be used as starting substances in process (b) according to the invention for the preparation of the compounds of the general formula (I). In formula (III), $Q^1$, $Q^2$, $R^1$, $R^2$ and Ar preferably or in particular have those meanings which have already been mentioned above as preferred or as particularly preferred for $Q^1$, $Q^2$, $R^1$, $R^2$ and Ar in connection with the description of the compounds of the formula (I).

The starting substances of the formula (III) are not yet known from the literature; however, they are the subject of a prior application which has not previously been published (cf. DE 4424787).

The aryliminoheterocyclic compounds of the formula (III) are obtained when aryl(thio)semicarbazides of the general formula (VI) are reacted with reactive carbonic acid derivatives, such as, for example, phosgene or thiophosgene, if appropriate in the presence of diluents, such as, for example, toluene and/or methylene chloride, at temperatures of between 0° and 200° C.

Formulae (Ia) and (Ib) provide general definitions of the compounds to be used, if appropriate, as starting substances, in process (b) according to the invention for the preparation of the compounds of the general formula (I). In formulae (Ia) and (Ib), $Q^1$, $Q^2$, $R^1$, $R^2$ and Ar preferably or in particular have those meanings which have already been mentioned above as preferred or as particularly preferred for $Q^1$, $Q^2$, $R^1$, $R^2$ and Ar in connection with the description of the compounds of the formula (I).

The compounds of the formula (Ia) or (Ib) are obtained when N-aryl nitrogen-containing heterocyclic compounds of the general formula (I) in which at least one of the groups $R^1$ or $R^2$ represents hydrogen are reacted with alkylating or acylating agents of the formulae (IXa or (IXb)

   (XIVa)

   (XIVb)

in which $R^1$ and $R^2$ have the abovementioned meanings, with the exception of hydrogen, and X represents halogen—preferably chlorine, bromine or iodine—or one of the groupings —O—SO$_2$—R$^1$ or —O—SO$_2$—R$^2$, if appropriate in the presence of a diluent and if appropriate in the presence of a reaction auxiliary at temperatures of between 0° C. and 80° C. (cf. the preparation examples).

The same diluents and reaction auxiliaries as in process (a) according to the invention are preferably possible here.

If appropriate, process (b) according to the invention is carried out in the presence of a reaction auxiliary. The same reaction auxiliaries as in process (a) according to the invention, but furthermore in addition also alkali metal sulfides, such as, for example, sodium sulfide or potassium sulfide, are possible here.

Process (b) according to the invention is preferably carried out using a diluent. The same diluents as in process (a) according to the invention are possible here.

The reaction temperatures can be varied within a substantial range when carrying out process (b) according to the invention. The process is in general carried out at temperatures of between 0° C. and +250° C., preferably at temperatures of between 20° C. and 150° C.

Process (b) according to the invention is in general carried out under normal pressure. However, it is also possible to carry out the process under increased or reduced pressure—in general between 0.1 bar and 10 bar.

For carrying out process (b) according to the invention, the starting substances of the formula (III) or of the formulae (Ia) or (Ib)—are in general initially introduced into the reaction vessel in a suitable diluent and are stirred at the required temperature until the reaction has ended. Working up can be carried out in the customary manner.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver Centaurea, Trifolium, Ranunculus, Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinchloa, Setaria, Panicum, Digitaria, Phleum, Poa, Festuca, Eleusine, Brachiaria, Lolium, Bromus, Avena, Cyperus, Sorghum, Agropyron Cynodon, Monochoria, Fimbristylis, Sagittaria, Eleocharis, Scirpus, Paspalum, Ischaemum, Sphenoclea, Dartyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating monocotyledon and dicotyledon weeds in monocotyledon cultures both by the pre-emergence and by the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents card for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor, dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzo-quat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents for improving soil structure is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha The preparation and use of the active compounds according to the invention can be seen from the following examples.

PREPARATION EXAMPLES

Example 1

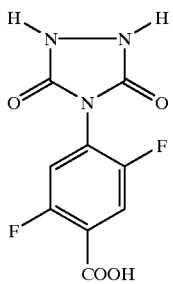

20.2 g (75 mmol) of 4-(4-cyano-2,5-difluoro-phenyl)-1-ethoxycarbonyl-semicarbazide are stirred in 50 ml of 25% strength aqueous potassium hydroxide solution at 80° C. for 2 hours. After the mixture has been cooled to 20° C., it is brought to pH=4 with concentrated hydrochloric acid and the product obtained as crystals is isolated by filtration.

16.0 g (90% of theory) of 4-(4-carboxy-2,5-difluorophenyl)-1,2,4-triazoline-2,5-dione of melting point >250° C. are obtained.

Example 2

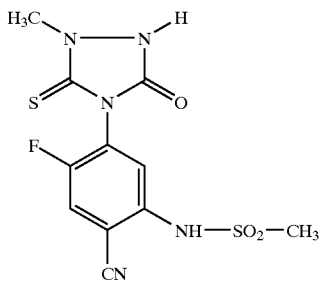

A mixture of 3.90 g (10 mmol) of 4-(4-cyano-2-fluoro-5-methylsulfonylaminophenyl)-2-methyl-1-ethoxycarbonyl-thiosemicarbazide, 8.10 g (80 mmol) of triethylamine and 100 ml of acetonitrile is stirred at the reflux temperature for 12 hours. The solvent is removed in vacuo, the residue is stirred with water, the mixture is acidified with concentrated hydrochloric acid and the product obtained as crystals is isolated by filtration.

1.20 g (35% of theory) of 4-(4-cyano-2-fluoro-5-methylsulfonylaminophenyl)-1-methyl-5-thioxo-1,2,4-triazolin-3-one of melting point >250° C. are obtained.

Example 3

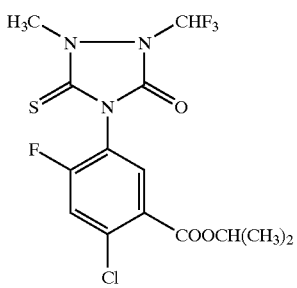

A mixture of 5.2 g (15 mmol) of 4-(4chloro-2-fluoro-5-i-propoxycarbonyl-phenyl-1-methyl-5-thioxo-1,2,4-triazolin-3-one, 5.2 g (37.5 mmol) of potassium carbonate and 50 ml of acetonitrile is stirred at 60° C. for 60 minutes; Frigen ($CHClF_2$) is then passed in at 60° C. for 6 hours. The mixture is subsequently concentrated under reduced pressure the residue is taken up in water, the mixture is acidified with concentrated hydrochloric acid and extracted with methylene chloride, and the organic phase is dried over sodium sulfate and filtered. The filtrate is concentrated and the crude product obtained in the residue is purified by column chromatography (silica gel, hexane/ethyl acetate, Vol.: 7:1).

0.7 g (12% of theory) of 4-(4chloro-2-fluoro-5-i-propoxycarbonyl-phenyl)-1-methyl-2-difluoromethyl-5-thioxo-1,2,4-triazolin-3-one of melting point 51° C. is obtained.

Example 4

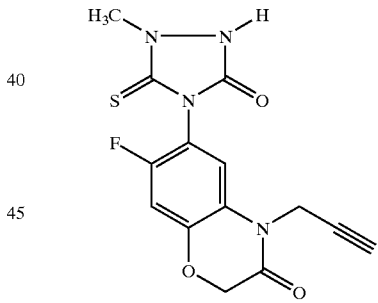

A mixture of 7.6 g (23 mmol) of 2-(7-fluoro-3,4-dihydro-3-oxo-4-propargyl-(2H)-1,4-bezoxazin-6-yl-imino)-3-methyl-3,4-dihydro-5-oxo-(4H)-1,3,4-thiadiazole and 20 ml of dimethyl sulfoxide is heated at 50° C. for 2 hours, at 70° C. for a further 2 hours and at 80° C. for a liter 2 hours. It is then concentrated under reduced pressure, the residue is stirred with water and the product obtained as crystals is isolated by filtration.

6.6 g (85% of theory) of 4-(7-fluoro-3,4-dihydro-3-oxo-4-propargyl-(2H)-1,4-benzoxazin-6-yl)-1-methyl-5-thioxo-1,2,4-triazolin-3-one of melting point 190° C. are obtained.

The compounds of the formula (I) listed in the following Table 1, for example, can also be prepared analogously to Examples 1 to 4 and in accordance with the general description of the preparation processes according to the invention.

TABLE 1
Examples of the compounds of the formula (I)
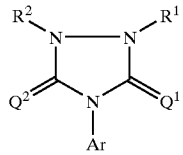
| Example No. | Q¹ | Q² | R¹ | R² | Ar | Physical data |
|---|---|---|---|---|---|---|
| 5 | O | O | H | CH₃ | 4-F, 2-OCH₃, 1-CN, 5-methyl phenyl | M.p.: 234° C. |
| 6 | S | O | CH₃ | H | 5-F, 2-F, 1-CN, 4-methyl phenyl | M.p.: 224° C. |
| 7 | S | O | CH₃ | CHO | 5-F, 2-F, 1-CN, 4-methyl phenyl | M.p.: 95° C. |
| 8 | O | S | H | CH₃ | 4-F, 2-O-CH(CH₃)C≡CH, 1-CN, 5-methyl phenyl | M.p.: 172° C. |
| 9 | S | O | CH₃ | CHF₂ | 7-F, 6-methyl, 4-propargyl benzoxazin-3-one | M.p.: 183° C. |
| 10 | S | O | CH₃ | CH₃ | 4-F, 2-Cl, 5-methyl, 1-COOCH(CH₃)₂ phenyl | M.p.: 118° C. |

TABLE 1-continued
Examples of the compounds of the formula (I)
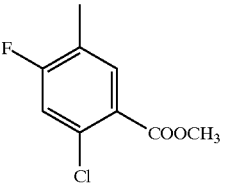
| Example No. | Q¹ | Q² | R¹ | R² | Ar | Physical data |
|---|---|---|---|---|---|---|
| 11 | S | O | CH$_3$ | H | 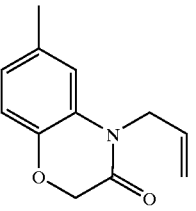 | M.p.: 139° C. |
| 12 | S | O | CH$_3$ | CH$_3$ | 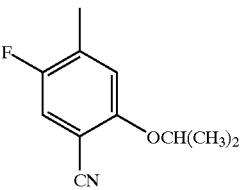 | M.p.: 227° C. |
| 13 | S | S | CH$_3$ | CH$_3$ | 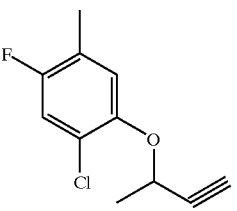 | M.p.: 175° C. |
| 14 | S | O | CH$_3$ | CHF$_2$ | 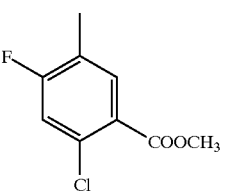 | M.p.: 122° C. |
| 15 | S | O | CH$_3$ | CHF$_2$ | 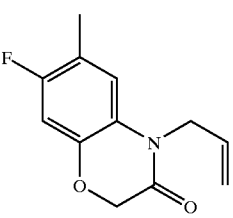 | M.p.: 64° C. |
| 16 | S | S | CH$_3$ | CH$_3$ |  | M.p.: 155° C. |

TABLE 1-continued
Examples of the compounds of the formula (I)
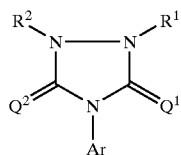
| Example No. | $Q^1$ | $Q^2$ | $R^1$ | $R^2$ | Ar | Physical data |
|---|---|---|---|---|---|---|
| 17 | S | S | $CH_3$ | $CH_3$ | | M.p.: 70° C. |
| 18 | S | S | $CH_3$ | $CH_3$ | | M.p.: 198° C. |
| 19 | S | S | $CH_3$ | $CH_3$ | | M.p.: — |
| 20 | S | S | $C_2H_5$ | $C_2H_5$ | | M.p.: 120° C. |
| 21 | S | S | $CH_3$ | $CH_3$ | | M.p.: 228° C. |

TABLE 1-continued

Examples of the compounds of the formula (I)

(I)

| Example No. | $Q^1$ | $Q^2$ | $R^1$ | $R^2$ | Ar | Physical data |
|---|---|---|---|---|---|---|
| 22 | S | S | $CH_3$ | $CH_3$ | (4-fluoro-2-chloro-5-methylphenyl isopropyl benzoate) | M.p.: 146° C. |
| 23 | S | S | $C_2H_5$ | $C_2H_5$ | (4-fluoro-2-chloro-5-methylphenyl but-3-yn-2-yl ether) | M.p.: 142° C. |
| 24 | S | S | $CH_3$ | $CH_3$ | (6-methyl-2,2,3,3-tetrafluoro-1,4-benzodioxine) | M.p.: 192° C. |
| 25 | S | S | $C_2H_5$ | $C_2H_5$ | (6-methyl-2,2,3,3-tetrafluoro-1,4-benzodioxine) | M.p.: 149° C. |
| 26 | S | S | $C_2H_5$ | $C_2H_5$ | (7-fluoro-6-methyl-4-allyl-2H-1,4-benzoxazin-3(4H)-one) | M.p.: 195° C. |

TABLE 1-continued
Examples of the compounds of the formula (I)
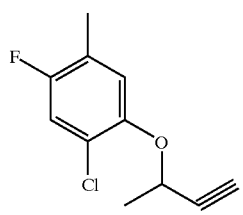
| Example No. | Q¹ | Q² | R¹ | R² | Ar | Physical data |
|---|---|---|---|---|---|---|
| 27 | S | S | $C_2H_5$ | $C_2H_5$ | 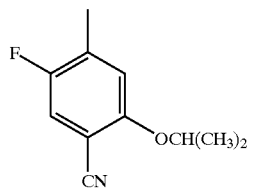 | M.p.: 148° C. |
| 28 | S | S | $C_2H_5$ | $C_2H_5$ | 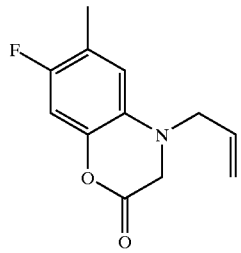 | M.p.: 133° C. |
| 29 | S | S | $C_2H_5$ | $C_2H_5$ | 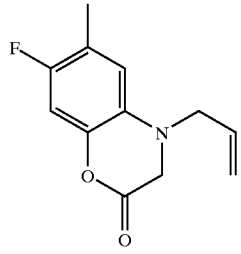 | |
| 30 | S | S | $CH_3$ | $CH_3$ | | |
| 31 | S | S | $C_2H_5$ | $C_2H_5$ | 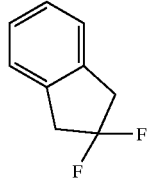 | M.p.: 197° C. |
| 32 | S | S | $CH_3$ | $CH_3$ | 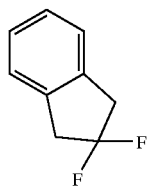 | M.p.: 229° C. |

TABLE 1-continued

Examples of the compounds of the formula (I)

$$\text{(I)}$$

| Example No. | $Q^1$ | $Q^2$ | $R^1$ | $R^2$ | Ar | Physical data |
|---|---|---|---|---|---|---|
| 33 | S | S | $CH_3$ | $CH_3$ | 4-F, 2-Cl, 5-methyl phenyl with -C(O)O-$C_2H_5$ | M.p.: 174° C. |
| 34 | S | S | $C_2H_5$ | $C_2H_5$ | 4-F, 2-Cl, 5-methyl phenyl with -C(O)O-$C_2H_5$ | M.p.: 103° C. |
| 35 | S | S | $CH_3$ | $CH_3$ | 7-F, 6-methyl-4-(prop-2-ynyl)-3-oxo-benzoxazine | M.p.: 259° C. |
| 36 | S | S | $C_2H_5$ | $C_2H_5$ | 7-F, 6-methyl-4-(prop-2-ynyl)-3-oxo-benzoxazine | M.p.: 248° C. |
| 37 | S | S | $CH_3$ | $CH_3$ | 4-F, 2-F, 5-methyl, CN phenyl | M.p.: 251° C. |
| 38 | O | S | H | $CH_3$ | 4-F, CN, 5-methyl phenyl with -NH-$SO_2C_2H_5$ | M.p.: 201° C. |

TABLE 1-continued

Examples of the compounds of the formula (I)

$$\text{(I)}$$

| Example No. | $Q^1$ | $Q^2$ | $R^1$ | $R^2$ | Ar | Physical data |
|---|---|---|---|---|---|---|
| 39 | O | S | CHO | $CH_3$ | 4-F, 2-(but-3-yn-2-yloxy), 6-CN, 5-methyl phenyl | M.p.: 75° C. |
| 40 | O | O | $CHF_2$ | $CH_3$ | 4-F, 2-(but-3-yn-2-yloxy), 6-Cl, 5-methyl phenyl | M.p.: 70° C. |
| 41 | O | S | $CH_3$ | $CH_3$ | 4-F, 2-(but-3-yn-2-yloxy), 6-CN, 5-methyl phenyl | M.p.: 157° C. |
| 42 | O | S | $CH_3$ | $CH_3$ | 4-F, 2-CN, 6-(NHSO$_2$C$_2$H$_5$), 5-methyl phenyl | M.p.: 250° C. |
| 43 | O | S | $CHF_2$ | $CH_3$ | 2-Cl, 3-(SO$_2$C$_2$H$_5$), 5-methyl phenyl | M.p.: 127° C. |
| 44 | O | S | $CH_3$ | $CH_3$ | 2-Cl, 3-(SO$_2$C$_2$H$_5$), 5-methyl phenyl | M.p.: 58° C. |

TABLE 1-continued
Examples of the compounds of the formula (I)
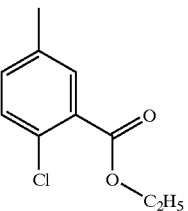
| Example No. | Q¹ | Q² | R¹ | R² | Ar | Physical data |
|---|---|---|---|---|---|---|
| 45 | O | S | CH₃ | CH₃ | 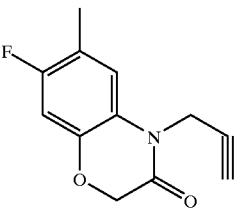 | M.p.: 138° C. |
| 46 | O | S | CH₃ | CH₃ | 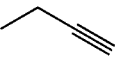 | M.p.: 236° C. |
| 47 | O | S | 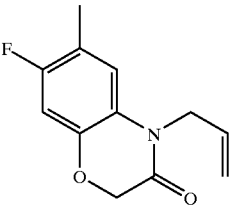 | CH₃ | 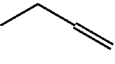 | M.p.: 122° C. |
| 48 | O | S | 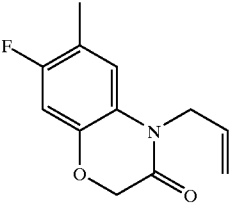 | CH₃ | 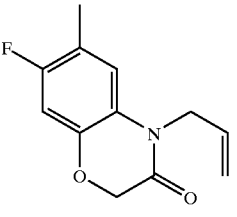 | |
| 49 | O | S | —CH₂CF₃ | CH₃ | 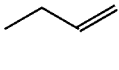 | M.p.: 135° C. |
| 50 | O | S | 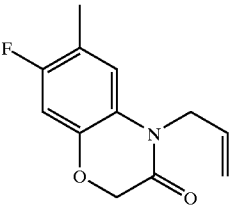 | CH₃ | | M.p.: 42° C. |

TABLE 1-continued

Examples of the compounds of the formula (I)

(I)

| Example No. | $Q^1$ | $Q^2$ | $R^1$ | $R^2$ | Ar | Physical data |
|---|---|---|---|---|---|---|
| 51 | O | S | CH$_3$ | CH$_3$ | 7-fluoro-6-methyl-4-allyl-benzoxazin-3-one | M.p.: 163° C. |
| 52 | O | S | CHF$_2$ | CH$_3$ | 7-fluoro-6-methyl-4-allyl-benzoxazin-3-one | M.p.: 176° C. |
| 53 | O | S | CH$_3$ | CH$_3$ | 2,5-difluoro-4-methyl-cyanophenyl | M.p.: 150° C. |
| 54 | O | S | H | CH$_3$ | 2-chloro-4-fluoro-5-methyl-benzoic acid isopropyl ester | M.p.: 67° C. |
| 55 | O | S | H | H | 2,5-difluoro-4-methyl-cyanophenyl | M.p.: 250° C. |

TABLE 1-continued

Examples of the compounds of the formula (I)

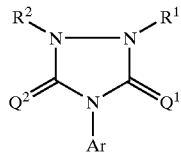

| Example No. | Q¹ | Q² | R¹ | R² | Ar | Physical data |
|---|---|---|---|---|---|---|
| 56 | O | S | H | CH$_3$ | (4-allyl-7-fluoro-3-oxo-3,4-dihydro-2H-1,4-benzoxazin-6-yl, methyl-substituted) | |
| 57 | O | O | —CH$_2$CH$_2$CH$_2$F | —CH$_2$CH$_2$CH$_2$F | (4-fluoro-2-chloro-5-(NHSO$_2$C$_2$H$_5$)-methylphenyl) | $n_d^{20}$ = 1.5442 |
| 58 | O | O | —CH$_2$CH$_2$CH$_2$F | —CH$_2$CH$_2$CH$_2$F | (4-fluoro-2-chloro-5-(O-propargyl)-methylphenyl) | $n_d^{20}$ = 1.5349 |
| 59 | O | O | —CH$_2$CH$_2$CH$_2$F | CH$_3$ | (4-fluoro-2-chloro-5-(O-propargyl)-methylphenyl) | $n_d^{20}$ = 1.5600 |
| 60 | O | O | —CH$_2$CH$_2$CH$_2$F | —CH$_2$CH$_2$CH$_2$F | (2-fluoro-4-chloro-methylphenyl) | |
| 61 | O | O | H | CH$_3$ | (2,5-difluoro-4-methyl-6-COOH-phenyl) | M.p.: 215° C. |

TABLE 1-continued

Examples of the compounds of the formula (I)

$$\text{(I)}$$

Structure: 1,2,4-triazolidine-3,5-dione ring with R² on one N, R¹ on the other N, Q² and Q¹ as the carbonyl substituents, and Ar on the middle N.

| Example No. | Q¹ | Q² | R¹ | R² | Ar | Physical data |
|---|---|---|---|---|---|---|
| 62 | O | O | H | CH₃ | 4-methyl-2,5-difluorophenyl with –C(O)Cl | M.p.: 250° C. |
| 63 | O | O | H | CH₃ | 4-methyl-2,5-difluorophenyl with –C(O)OCH₃ | M.p.: 156° C. |
| 64 | O | O | H | CH₃ | 4-methyl-2,5-difluorophenyl with –C(O)OC₂H₅ | ¹H—NMR (CDCl₃): 3.25, 4.40–4.46, 7.22–7.24 ppm |
| 65 | O | S | H | CH₃ | 4-methyl-5-fluoro-2-(NH-SO₂C₂H₅)-phenyl with COOH | M.p.: 210° C. |
| 66 | O | O | H | CH₃ | 4-methyl-2,5-difluorophenyl with –C(O)NH₂ | M.p.: 163° C. |
| 67 | O | S | H | CH₃ | 4-methyl-2,5-difluorophenyl with COOH | M.p.: 143° C. |

TABLE 1-continued
Examples of the compounds of the formula (I)
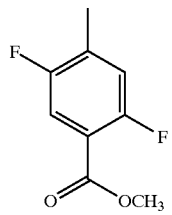
(I)
| Example No. | Q¹ | Q² | R¹ | R² | Ar | Physical data |
|---|---|---|---|---|---|---|
| 68 | O | S | H | CH₃ | 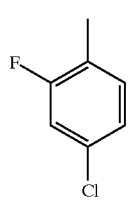 | M.p.: 158° C. |
| 69 | O | S | H | CH₃ | 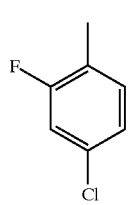 | M.p.: 75° C. |
| 70 | O | S | CH₃ | CH₃ | 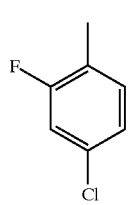 | ¹H—NMR (CDCl₃) 3.45, 3.73, 7.30–7.40 ppm |
| 71 | O | S | CH₃ | CH₃ | 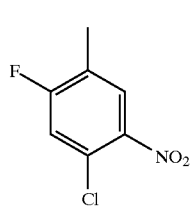 | M.p.: 146° C. |
| 72 | O | S | CH₃ | CH₃ | 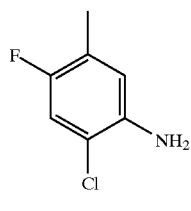 | M.p.: 208° C. |
| 73 | O | S | CH₃ | CH₃ | 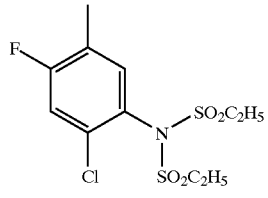 | M.p.: 195° C. |

TABLE 1-continued

Examples of the compounds of the formula (I)

(I)

| Example No. | $Q^1$ | $Q^2$ | $R^1$ | $R^2$ | Ar | Physical data |
|---|---|---|---|---|---|---|
| 74 | O | O | H | CH$_3$ | 4-chloro-2-fluorophenyl (with methyl) | (amorphous) |
| 75 | O | O | H | H | 2,5-difluoro-4-(ethoxycarbonyl)phenyl (with methyl) | M.p.: 150° C. |
| 76 | O | O | CH$_3$ | CH$_3$ | 2,5-difluoro-4-(ethoxycarbonyl)phenyl (with methyl) | M.p.: 101° C. |
| 77 | O | S | CH$_2$CH=CH$_2$ | CH$_3$ | 7-fluoro-6-methyl-4-(prop-2-ynyl)-3-oxo-benzoxazinyl | M.p.: 172° C. |
| 78 | O | S | CH$_2$CH=CH$_2$ | CH$_3$ | 7-fluoro-6-methyl-4-(prop-2-ynyl)-3-oxo-benzoxazinyl | M.p.: 199° C. |
| 79 | O | S | H | CH$_3$ | 2-chloro-4-fluoro-5-methyl-phenoxy-acetic acid methyl ester | amorphous |

TABLE 1-continued
Examples of the compounds of the formula (I)
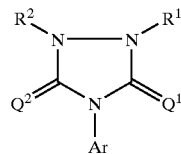
(I)
| Example No. | Q¹ | Q² | R¹ | R² | Ar | Physical data |
|---|---|---|---|---|---|---|
| 80 | S | S | CH₃ | CH₃ | 4-F-2-Cl-phenoxy-CH₂-C(O)-OCH₃ | M.p.: 160° C. |
| 81 | O | S | H | CH₃ | 4-F-2-Cl-phenoxy-CH₂-C(O)-OC₂H₅ | amorphous |
| 82 | O | S | CHF₂ | CH₃ | 4-F-2-Cl-phenoxy-CH₂-C(O)-OCH₃ | M.p.: 99° C. |
| 83 | O | S | CH₃ | CH₃ | 4-F-2-Cl-phenoxy-CH₂-C(O)-OCH₃ | |
| 84 | S | S | CH₃ | CH₃ | 4-F-2-Cl-phenoxy-CH₂-C(O)-OC₂H₅ | M.p.: 131° C. |

TABLE 1-continued

Examples of the compounds of the formula (I)

(I)

$$\begin{array}{c} R^2\diagdown N\text{---}N\diagup R^1 \\ Q^2 \diagup\diagdown N \diagdown Q^1 \\ | \\ Ar \end{array}$$

| Example No. | Q¹ | Q² | R¹ | R² | Ar | Physical data |
|---|---|---|---|---|---|---|
| 85 | O | S | CHF₂ | CH₃ | (4-F, 2-Cl, 5-OCH₂C(O)OC₂H₅ phenyl) | |
| 86 | O | S | C₂H₅ | CH₃ | (benzoxazinone with propargyl and F) | |

The compound listed as Example 13 in Table 1 can be prepared, for example, as follows:

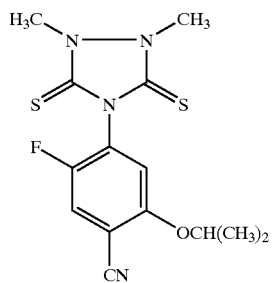

A mixture of 1.0 g (0.3 mmol) of 2-(4-cyano-2-fluoro-4-i-propoxy-phenylimino)-3,4-dihydro-3,4-methyl-5-thioxo (4H)-1,3,4-thiadiazole, 0.1 g (0.1 mmol) of sodium sulfide and 20 ml of ethanol is heated under reflux for about 20 hours. It is then concentrated, the residue is taken up in methylene chloride and the mixture is washed with water, dried with sodium sulfate and filtered. The filtrate is concentrated, the residue is digested with diethyl ether and the product obtained as crystals is isolated by filtration.

0.25 g (25% of theory) of 4-(4-cyano-2-fluoro-5-i-propoxy-phenyl)-1,2-dimethyl-1,2,4-triazoline-2,5-dithione of melting point 175° C. is obtained.

The compound listed as Example 21 in Table 1 can be prepared, for example, as follows:

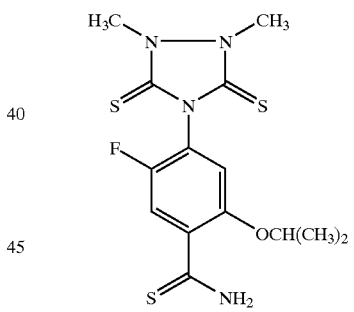

Hydrogen sulfide is passed into a mixture of 0.9 g (2.6 mmol) of 4-(4-cyano-2-fluoro-5-i-propoxy-phenyl)-1,2-dimethyl-1,2,4-triazoline-2,5-dithione, 2 ml (14 mmol) of triethylamine and 20 ml of pyridine at 90° C. for 9 hours. After the mixture has been cooled, the solvent is stripped off on a rotary evaporator and the residue is stirred with 2 normal hydrochloric acid. The crude product is filtered off with suction, washed with water, dried and purified by column chromatography (mobile phase: hexane/ethyl acetate 4:1).

0.42 g (43% of theory) of 4-(2-fluoro-5-i-propoxy-4-thiocarbamoylphenyl)-1,2-dimethyl-1,2,4-triazoline-2,5-dithione of melting point 228° C. is obtained.

The compound listed as Example 46 in Table 1 can be prepared, for example, as follows:

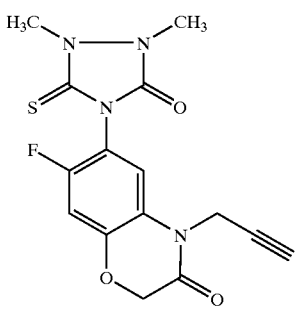

A solution of 2.1 g (6 mmol) of 4-(7-fluoro-3,4-dihydro-3-oxo-4-propargyl-(2H)-1,4-benzoxazin-6-yl)-1-methyl-5-methylthio-1,2,4-triazolin-3-one in 20 ml of dimethylformamide is heated under reflux for 16 hours. It is then concentrated under a water pump vacuum and the residue is purified by column chromatography.

0.9 (43% of theory) of 4-(7-fluoro-3,4-dihydro-3-oxo-4-propargyl-(2H)-1,4-benzoxazin-6-yl)-1,2-dimethyl-5-thioxo-1,2,4-triazolin-3-one of melting point 236° C. is obtained.

The compound listed as Example 61 in Table 1 can be prepared, for example, as follows:

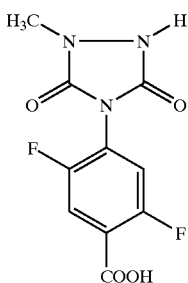

44.7 g (0.15 mol) of 4-(4-cyano-2,5-difluoro-phenyl)1-ethoxycarbonyl-2-methyl-semicarbazide are stirred in 200 ml of 4 molar aqueous potassium hydroxide solution at 80° C. for 30 minutes. After the mixture has been cooled to 20° C., it is brought to pH=4 with concentrated hydrochloric acid and the product obtained as crystals is isolated by filtration.

36 g (95% of theory) of 4-(4-carboxy-2,5-difluoro-phenyl)-1-methyl-1,2,4-triazoline-3,5-dione of melting point 215° C. are obtained The compound listed as Example 62 in Table 1 can be prepared, for example, as follows:

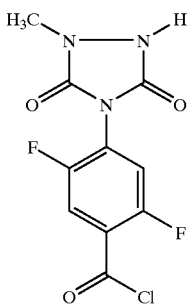

27.1 g (0.1 mol) of 4-(4carboxy-2,5-difluoro-phenyl)-1-methyl-1,2,4-triazole-3,5-dione are heated to 80° C. in 200 ml of toluene. 14.3 g (0.12 mol) of thionyl chloride are added dropwise at this tempera in the course of 30 minutes, and the mixture is heated to the reflux temperature and stirred for about 2 hours until the evolution of gas has ended. After the mixture has been cooled to 20° C., the product obtained as crystals is isolated by filtration.

7.2 g (25% of theory) of 4-(4-chlorocarbonyl-2,5-difluoro-phenyl)-1-methyl-1,2,4-triazole-3,5-dione of melting point >250° C. are obtained.

The compound listed as Example 63 in Table 1 can be prepared, for example, as follows:

6.5 g (0.024 mol) of 4-(4-carboxy-2,5-difluoro-phenyl)-1-methyl-1,2,4-triazole-3,5-dione are stirred at the reflux temperature with 200 ml of methanol and two drops of sulfuric acid for 8 hours. After the mixture has been cooled to 20° C., it is concentrated under a water pump vacuum, the residue is dissolved in methylene chloride, the solution is washed with water and the organic phase is dried over sodium sulfate and freed thoroughly from the solvent under a water pump vacuum.

4.2 g (62% of theory) of 4-(4-methoxycarbonyl-2,5-difluoro-phenyl)-1-methyl-1,2,4-triazole-3,5-dione of melting point 156° C. are obtained.

The compound listed as Example 69 in Table 1 can be prepared, for example, as follows:

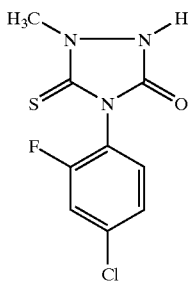

29.3 g (0.096 mol) of 4-(4-chloro-2-fluoro-phenyl)-2-methyl-1-ethoxycarbonyl-thiosemicarbazide are stirred at the reflux temperature in 400 ml of acetonitrile with 78 g (0.77 mol) of triethylamine for 8 hours and, after the mixture has been cooled, it is concentrated under a water pump vacuum Water is added to the residue, the mixture is brought to pH=4 with concentrated hydrochloric acid and extracted with methylene chloride, and the organic phase is separated off, dried over sodium sulfate and concentrated under a water pump vacuum.

22 g (88% of theory) of 4-(4-chloro-2-fluoro-phenyl)-1-methyl-5-thioxo-1,2,4-triazol-3-one of melting point 75° C. are obtained.

The compound listed as Example 70 in Table 1 can be prepared, for example, as follows:

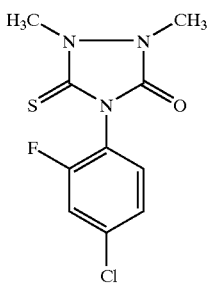

7.1 g (0.026 mol) of the meso ionic compound according to Example (Ia-5)—below—are stirred under reflux in 100 ml of dimethylformamide for 18 hours and, after the mixture has been cooled, it is concentrated under a water pump vacuum.

5.9 g (83% of theory) of 4-(4-chloro-2-fluoro-phenyl)-1,2-diethyl-5-thioxo-1,2,4-triazol-3-one are obtained.

$^1$H-NMR (CDCl$_3$): 3.45; 3.73; 7.30–7.40 ppm.

The compound listed as Example 71 in Table 1 can be prepared, for example, as follows:

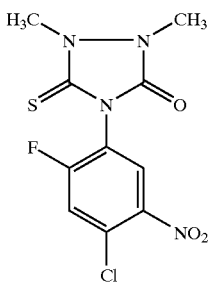

4.65 g (0.017 mol) of 4-(4-chloro-2-fluoro-phenyl)-1,2-dimethyl-5-thioxo-1,2,4-triazol-3-one are initially introduced into the reaction vessel in 30 ml of concentrated sulfuric acid, and 3 ml of 98% strength nitric acid are added dropwise at 0° C. The mixture is subsequently stirred at room temperature for 8 hours and stirred with ice water and the product which has precipitated out is filtered off.

2.9 g (54% of theory) of 4-(4-chloro-2-fluoro-5-nitro-phenyl)-1,2-dimethyl-5-thioxo-1,2,4-triazol-3-one of melting point 146° C. are obtained.

The compound listed as Example 72 in Table 1 can be prepared, for example, as follows:

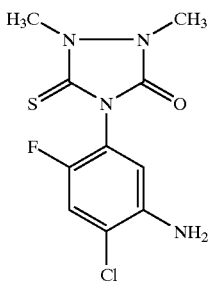

2.6 g (0.008 mol) of 4-(4-chloro-2-fluoro-5-nitro-phenyl)-1,2-dimethyl-5-thioxo-1,2,4-triazol-3-one are initially introduced into the reaction vessel in 20 ml of acetic acid with 10 ml of water and 10 ml of ethyl acetate, and 4.6 g (0.0082 mol) of iron powder are added in portions, the temperature being kept at maximum of 45° C. using an ice-bath. When the addition has ended, the mixture is subsequently stirred at 23° C. for 2 hours and filtered with suction and the residue is washed with water, The filtrate is extracted with ethyl acetate and the organic phase is washed with sodium hydrogencarbonate solution, dried over sodium sulfate and concentrated under a water pump vacuum.

1.5 g (65% of theory) of 4-(4-chloro-2-fluoro-5-amino-phenyl-1,2-dimethyl-5-thioxo-1,2,4-triazol-3-one of melting point 208° C. are obtained.

The compound listed as Example 73 in Table 1 can be prepared, for example, as follows:

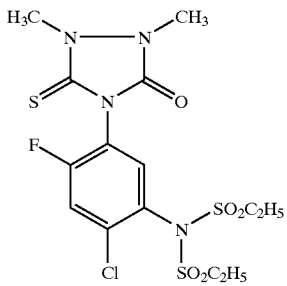

1.8 g (0.018 mol) of triethylamine and then 2.3 g (0.018 mol) of ethanesulfonyl chloride are added to 1.3 g (0.0045 mol) of 4-(4-chloro-2-fluoro-5-amino-phenyl)-1,2-dimethyl-5-thioxo-1,2,4-triazol-3-one in 50 ml of methylene chloride at −10° C., the mixture is stirred at room temperature for 3 hours, water is added and the organic phase is separated off, dried over sodium sulfate and concentrated under a water pump vacuum.

2.0 g (94% of theory) of 4-[4-chloro-2-fluoro-5-(diethylsulfonyl)-amino-phenyl]-1,2-dimethyl-5-thioxo-1,2,4-triazol-3-one of melting point 195° C. (decomposition) are obtained.

Compounds of the Formulae (Ia) or (Ib):

Example (Ia-1)

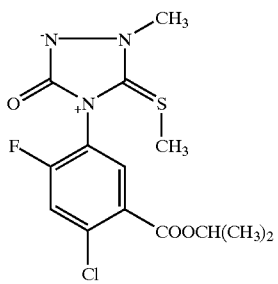

A mixture of 4.2 g (12 mmol) of 4-(4-chloro-2-fluoro-5-i-propoxycarbonyl-phenyl)-1-methyl-5-thioxo-1,2,4-triazolin-3-one, 3.5 g (25 mmol) of potassium carbonate, 2.2 g (15 mmol) of methyl iodide and 60 ml of acetonitrile is stirred at 40° C. for 12 hours. It is then concentrated, the residue is taken up in water, the mixture is acidified with concentrated hydrochloric acid and extracted with methylene chloride and the organic phase is dried with sodium sulfate and filtered. The filtrate is concentrated and the crude product obtained as the residue is purified by column chromatography (silica gel, methylene chloride/methanol, volume: 40:1).

1.0 g (24% of theory) of the compound of the structural formula given above of melting point 159° C. is obtained.

The compounds of the formula (Ia) listed in the following Table 2, for example, can also be prepared analogously.

TABLE 2

Examples of the compounds of the formula (Ia)

(Ia) structure: 1,2,4-triazole core with N—R¹, Q¹—R², Q², and Ar substituents (mesoionic).

| Example No. | Q¹ | Q² | R¹ | R² | Ar | Physical data |
|---|---|---|---|---|---|---|
| Ia-2 | S | O | CH₃ | CH₃ | 4-fluoro-2-methyl-phenyl bearing N-propargyl-3-oxo-1,4-benzoxazine moiety | M.p.: 237° C. |
| Ia-3 | S | O | CH₃ | CH₃ | 4-fluoro-2-methyl-6-chloro-phenyl with O—CH(CH₃)—C≡CH substituent | M.p.: 168° C. |
| Ia-4 | S | O | CH₃ | CH₃ | 4-fluoro-2-methyl-5-fluoro-6-cyano-phenyl | M.p.: 185° C. |
| Ia-5 | S | O | CH₃ | CH₃ | 4-chloro-2-fluoro-phenyl | M.p.: 182° C. |

The compound listed as Example (Ia-5) in Table 2 can be prepared, for example, as follows

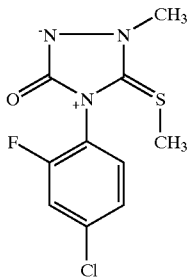

20.7 g (0.08 mol) of 4-(4-chloro-2-fluoro-phenyl)-1-methyl-5-thioxo-1,2,4-triazol-3-one are initially introduced into the reaction vessel with 150 ml of dimethyl sulfoxide and 22 g (0.16 mol) of potassium carbonate. 23 g (0.16 mol) of methyl iodide are then added dropwise at 0° C. in the course of 30 minutes. The mixture is subsequently stirred at 23° C. for 4 hours and then concentrated. The residue is stirred with water, the mixture is acidified with concentrated hydrochloric acid and extracted with methylene chloride, and the organic phase is dried over sodium sulfate and concentrated under a water pump vacuum. After the residue has been stirred with isopropanol, the product obtained as crystals is isolated by filtration.

7.8 g (36% of theory) of the mesoionic compound of the structure given above are obtained.

Starting substances of the formula (II):

Example (II-1)

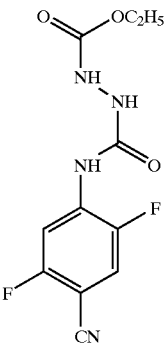

18.0 g (0.10 mol) of 4-cyano-2,5-difluoro-phenyl isocyanate are added to a solution of 10.4 g (0.10 mol) of ethyl carbazate in 100 ml of toluene at 10° C. and the mixture is stirred at 20° C. for 2 hours and then at the reflux temperature for a further 2 hours. The product obtained as crystals after cooling is isolated by filtration.

24.2 g (90% of theory) of 4-(4-cyano-2,5-difluoro-phenyl)-1-ethoxy-carbonyl-semicarbazide of melting point 245° C. are obtained.

Example (II-2)

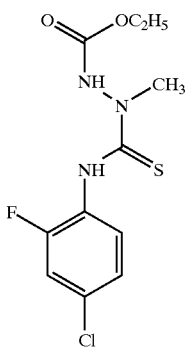

18.8 g (0.1 mol) of 4-chloro-2-fluoro-phenyl isothiocyanate are stirred at the reflux temperature in 200 ml of acetonitrile with 11.8 g (0.1 mol) of 2-methyl-1-ethoxy-carbonyl-hydrazine and 9.24 g (0.11 mol) of sodium hydrogencarbonate for 8 hours. After the mixture has been cooled, it is concentrated under a water pump vacuum, the residue is stirred with water, the mixture is extracted with methylene chloride and the organic phase is separated off, dried over sodium sulfate and concentrated under a water pump vacuum.

29 g (95% of theory) of 4-(4-chloro-2-fluoro-phenyl)-2-methyl-1-ethoxy-carbonyl-thiosemicarbazide of melting point 151° C. are obtained.

Starting substances of the formula (II):

Example (III-1)

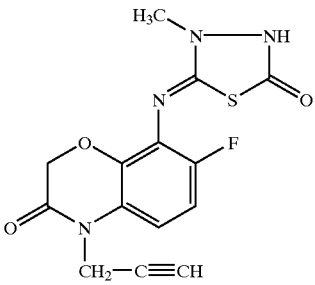

6 g (12 mmol) of a 20% strength solution of phosgene in toluene are added to a suspension of 3.1 g (10 mmol) of 2-methyl-4-(7-fluoro-3,4-dihydro-3-oxo 4-propargyl-(2H)-1,4-benzoxazin-6-yl)-thiosemicarbazide in 50 ml of methylene chloride at about 20° C. The reaction mixture is heated at 40° C. for about 15 hours, the solvent is removed in vacuo and the residue is taken up in water. The mixture is neutralized with sodium bicarbonate solution and the solid is filtered off, washed with water and dried in vacuo at 40–50° C.

2.8 g (84% of theory) of 2-(7-fluoro-3,4-dihydro-3-oxo-4-propargyl-(2H)-1,4-benzoxazin-6-yl-imino)-3-methyl-3,4-dihydro-5-oxo-(4H)-1,3,4-thiadiazole are obtained.

Melting point: 214° C.

Example (III-2)

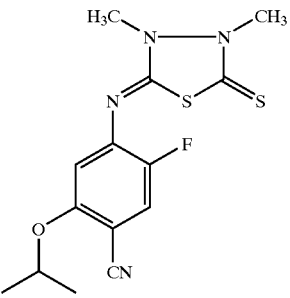

0.66 g (5.7 mmol) of thiophosgene is added to a solution of 1.7 g (5.7 mmol) of 4-(4-cyano-2-fluoro-5-i-propoxy-phenyl)-1,2-dimethylthiosemicarbazide in 30 ml of dry methylene chloride. The reaction is slightly exothermic. The reaction mixture is stirred at the reflux temperature for 4 hours, the solvent is removed in vacuo and the residue is stirred with saturated sodium carbonate solution. The solid which forms is filtered off, washed with water and pressed off on clay.

1.5 g (78% of theory) of 2-(4-cyano-2-fluoro-5-i-propoxy-phenylimino)-3,4-dimethyl-5-thio-1,3,4-thiadiazole of melting point 117° are obtained.

Starting substances of the formula (IV):

Example (IV-1)

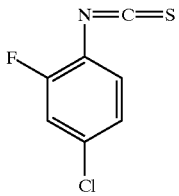

129 g (1.12 mol) of thiophosgene are added to 81 g (0.56 mol) of 4-chloro-2-fluoro-aniline in 500 ml of chlorobenzene at 80° C. to 90° C. in the course of 1 hour and the mixture is then stirred at the reflux temperature for 2 hours until the evolution of gas has ended. The clear solution is concentrated to dryness under a water pump vacuum.

102 g (97% of theory) of 4-chloro-2-fluoro-phenyl isothiocyanate are obtained $^1$H-NMR (CDCl$_3$): 7.10–7.20 ppm; GC-MS: (M=187) 98.4%.

Use Examples

Example A

Pre-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep an constant the amount of water per unit area The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the compounds according to preparation examples 3, 9, 10, 12, 13, 14 and 15, when applied in amounts of 60 g/ha, show in some cases a good tolerability toward crop plants, such as, for example, barley and corn (10–70%) and a very potent action against weeds, such as Alopecurus (90–100%), Cynodon (95–100%), Setaria (70–100%), Amaranthus (90–100%), Chenopodium (100%), Matricaria (95–100%), Polygonum (80–100%), Portulaca (95–100%) and Viola (90–100%).

Example B

Post-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit are& After three weeks, the degree of damage to the plants is rated in % damage in comparison to the development of the untreated control. The figures denote:

0%=no action (like untreated control)
100%=total destruction

In this test, for example, the compounds according to preparation examples 3, 4, 9, 10, 12, 13, 14 and 15 and Ia-1 and Ia-2, when applied in amounts of between 15 and 250 g/ha, show a potent action against weeds, such as Amaranthus (60–100%), Chenopodium (90–100%), Datura (80–100%), Galium (90–100%) and Veronica (50–100%).

What is claimed is:

1. A substituted N-aryl nitrogen-containing heterocyclic compound of formula (I)

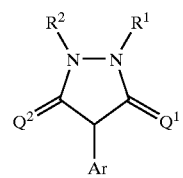

in which
  $Q^1$ represents oxygen or sulfur,
  $Q^2$ represents oxygen or sulfur,
  $R^1$ represents hydrogen, cyano or formyl, or represents $C_1$–$C_6$-alkyl, in each case optionally substituted by fluorine, chlorine, cyano, carboxyl, $C_1$–$C_4$-alkoxy, $C_3$–$C_4$-alkenyloxy, $C_3$–$C_4$-alkinyloxy, $C_1$–$C_4$-alkylthio, $C_3$–$C_4$-alkenylthio, $C_3$–$C_4$-alkinylthio, $C_1$–$C_4$-alkoxy-carbonyl, $C_3$–$C_4$-alkenyloxy-carbonyl or $C_3$–$C_4$-alkinyloxy-carbonyl,
  $R^1$ furthermore represents $C_3$–$C_6$-alkenyl or $C_3$–$C_6$-alkinyl, in each case optionally substituted by fluorine or chlorine,
  $R^1$ furthermore represents $C_1$–$C_6$-alkyl-carbonyl, $C_3$–$C_6$-alkenyl-carbonyl, $C_3$–$C_6$-alkinyl-carbonyl, $C_3$–$C_6$-alkoxy-carbonyl, $C_3$–$C_6$-alkenyloxy-carbonyl or $C_3$–$C_6$-alkinyloxy-carbonyl, in each case optionally substituted by fluorine or chlorine,
  $R^1$ furthermore represents $C_3$–$C_6$-cycloalkyl or $C_3$–$C_6$-cycloalkyl-carbonyl, in each case optionally substituted by fluorine, chlorine, bromine, cyano or carboxyl,
  $R^2$ represents hydrogen, cyano or formyl, or represents $C_1$–$C_6$-alkyl, in each case optionally substituted by fluorine, chlorine, cyano, carboxyl, $C_1$–$C_4$-alkoxy, $C_3$–$C_4$-alkenyloxy, $C_3$–$C_4$-alkinyloxy, $C_1$–$C_4$- alkylthio, $C_3$–$C_4$-alkenylthio, $C_3$–$C_4$-alkinylthio, $C_1$–$C_4$-alkoxy-carbonyl, $C_3$–$C_4$-alkenyloxy-carbonyl or $C_3$–$C_4$-alkinyloxy-carbonyl, $R^2$ furthermore represents $C_3$–$C_6$-alkenyl or $C_3$–$C_6$-alkinyl, in each case optionally substituted by fluorine or chlorine, $R^2$ furthermore represents $C_1$–$C_6$-alkyl-carbonyl, $C_3$–$C_6$-alkenyl-carbonyl, $C_3$–$C_6$-alkinyl-carbonyl, $C_1$–$C_6$-alkoxy-carbonyl, $C_3$–$C_6$-alkenyloxy-carbonyl or $C_3$–$C_6$-alkinyloxy-carbonyl, in each case optionally substituted by fluorine or chlorine, $R^2$ furthermore represents $C_3$–$C_6$-cycloalkyl or $C_3$–$C_6$cycloalkyl-carbonyl, in each case optionally substituted by fluorine, chlorine, bromine, cyano or carboxyl, and Ar represents:

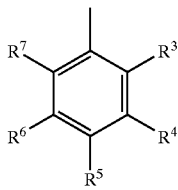

in which
$R^3$ represents hydrogen, fluorine, chlorine or bromine,
$R^4$ represents hydrogen, fluorine, chlorine or bromine,
$R^5$ and $R^6$ together represent —$Q^3$—C($R^8$, $R^9$)—$CQ^4$—N($R^{10}$)—,
in which
$Q^3$ and $Q^4$ are each oxygen,
$R^7$ represents hydrogen, fluorine, chlorine or bromine,
$R^8$ and $R^9$ are identical or different and individually represent hydrogen, fluorine, chlorine, bromine or $C_1$–$C_4$-alkyl or together represent $C_2$–$C_5$-alkanediyl, and
$R^{10}$ represents hydrogen or hydroxyl, or represents alkyl, alkylcarbonyl, alkoxycarbonyl or alkylsulfonyl having in each case 1 to 6 carbon atoms in the alkyl groups and in each case optionally substituted by cyano, fluorine, chlorine, $C_1$–$C_4$-alkoxy, $C_1$–$C_4$-alkyl-carbonyl or $C_1$–$C_4$-alkoxy-carbonyl,
furthermore represents alkenyl or alkinyl having in each case 2 to 6 carbon atoms and in each case optionally substituted by fluorine, chlorine or bromine,
$R^{10}$ furthermore represents cycloalkyl or cycloalkylalkyl having in each case 3 to 6 carbon atoms in the cycloalkyl groups and where appropriate 1 to 3 atoms in the alkyl group and in each case optionally substituted by fluorine, chlorine, bromine or $C_1$–$C_4$-alkyl,
$R^{10}$ furthermore represents alkoxy or alkenyloxy having in each case up to 6 carbon atoms and in each case optionally substituted by fluorine and/or chlorine, and
$R^{10}$ furthermore represents benzyl or benzyloxy, in each case optionally substituted by cyano, fluorine, chlorine, $C_1$–$C_4$-alkyl, $C_1$–$C_4$-halogenoalkyl, $C_1$–$C_4$-alkoxy or $C_1$–$C_4$-halogenoalkoxy.

2. The substituted N-aryl nitrogen-containing heterocyclic compound of claim 1, in which
$Q^1$ represents oxygen or sulfur,
$Q^2$ represents oxygen or sulfur,
$R^1$ represents hydrogen, cyano or formyl, or represents methyl, ethyl, N- or i-propyl or n- x-, s- or t-butyl, in each case optionally substituted by fluorine, chlorine, cyano, carboxyl, methoxy or ethoxy, $R^1$ furthermore represents propenyl, butenyl, propinyl or butinyl, in each case optionally substituted by fluorine or chlorine, $R^1$ furthermore represents acetyl, propionyl, methoxycarbonyl or ethoxycarbonyl, in each case optionally substituted by fluorine or chlorine, $R^1$ furthermore represents cyclopropyl which is optionally substituted by fluorine or chlorine, $R^2$ represents hydrogen, cyano or formyl, or represents methyl, ethyl, n- or i-propyl or n- i-, s- or t-butyl, in each case optionally substituted by fluorine, chlorine, cyano, carboxyl, methoxy or ethoxy, $R^2$ furthermore represents propenyl, butenyl, propinyl or butinyl, in each case optionally substituted by fluorine or chlorine, $R^2$ furthermore represents acetyl, propionyl, methoxycarbonyl or ethoxycarbonyl, in each case optionally substituted by fluorine or chlorine, $R^2$ furthermore represents cyclopropyl which is optionally substituted by fluorine or chlorine, and Ar represents:

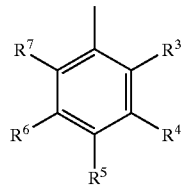

in which
$R^3$ represents hydrogen, fluorine or chlorine,
$R^4$ represents hydrogen, fluorine or chlorine,
$R^5$ and $R^6$ together represent —$O^3$—C($R^8$,$R^9$)—$CQ^4$—N($R^{10}$)—,
in which
$Q^3$ and $Q^4$ are each oxygen,
$R^7$ represents hydrogen, fluorine or chlorine,
$R^8$ and $R^9$ are identical or different and individually represent hydrogen, fluorine, chlorine, methyl or ethyl or together represent ethane-1,2-diyl-(dimethylene), and
$R^{10}$ represents hydrogen or hydroxyl, or represents methyl, ethyl, n- or i-propyl or n-, i-, s- or t-butyl which are optionally substituted by cyano, fluorine, chlorine, methoxy, ethoxy, acetyl, propionyl, methoxycarbonyl or ethoxy-carbonyl,
$R^{10}$ furthermore represents propenyl, butenyl, propinyl or butinyl, in each case optionally substituted by fluorine, chlorine or bromine,
$R^{10}$ furthermore represents cyclopropyl, cyclobutyl, cyclopentyl, cyclohexyl, cyclopropylmethyl, cyclobutylmethyl, cyclopentylmethyl or cyclohexylmethyl, in each case optionally substituted by fluorine, chlorine, bromine, methyl or ethyl,
$R^{10}$ furthermore represents methoxy, ethoxy, n- or i-propoxy, n-, i- or s-butoxy, propenyloxy or butenyloxy, in each case optionally substituted by fluorine and/or chlorine, and
$R^{10}$ furthermore represents benzyl or benzyloxy, in each case optionally substituted by cyano, fluorine, chlorine, methyl, ethyl, trifluoromethyl, methoxy, ethoxy, difluoromethyl or trifluoromethoxy.

3. The substituted N-aryl nitrogen-containing heterocyclic compound of claim 2, in which $R^4$ is hydrogen.

4. A herbicidal composition comprising of at least one compound of claim 1 and a herbicidally acceptable carrier.

5. A method of combating undesirable plants which comprises allowing an herbicidally effective amount of the composition of claim 4, to act on undesirable plants and/or their environment.

* * * * *